United States Patent
Torii et al.

(10) Patent No.: US 8,252,715 B2
(45) Date of Patent: Aug. 28, 2012

(54) WATER-ABSORBING AGENT AND PRODUCTION METHOD THEREOF

(75) Inventors: Kazushi Torii, Himeji (JP); Yoshifumi Adachi, Himeji (JP); Taishi Kobayashi, Himeji (JP); Yusuke Watanabe, Himeji (JP); Hiroyuki Ikeuchi, Himeji (JP); Toshimasa Kitayama, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 652 days.

(21) Appl. No.: 12/041,609

(22) Filed: Mar. 3, 2008

(65) Prior Publication Data

US 2008/0221229 A1 Sep. 11, 2008

(30) Foreign Application Priority Data

Mar. 5, 2007 (JP) ................................. 2007-054855
Sep. 28, 2007 (JP) ................................. 2007-254149
Sep. 28, 2007 (JP) ................................. 2007-256635

(51) Int. Cl.
*B01J 20/285* (2006.01)
*C08F 20/02* (2006.01)
*C08F 16/28* (2006.01)
*C08F 32/00* (2006.01)
*C08F 120/00* (2006.01)

(52) U.S. Cl. ......... 502/402; 521/56; 521/60; 525/329.7; 525/328.2; 525/330.3

(58) Field of Classification Search .................... 521/50, 521/56; 525/329.7, 328.2, 330.3
See application file for complete search history.

(56) References Cited

U.S. PATENT DOCUMENTS

| | | | |
|---|---|---|---|
| 5,633,316 A | 5/1997 | Gartner et al. | |
| 5,668,078 A | 9/1997 | Sumiya et al. | |
| 5,728,742 A | 3/1998 | Staples et al. | |
| 5,981,070 A * | 11/1999 | Ishizaki et al. | 428/407 |
| 6,414,214 B1 | 7/2002 | Engelhardt et al. | |
| 7,157,141 B2 | 1/2007 | Inger et al. | |
| 2002/0128618 A1 | 9/2002 | Frenz et al. | |
| 2004/0186239 A1 | 9/2004 | Qin et al. | |
| 2004/0265387 A1 | 12/2004 | Hermeling et al. | |
| 2005/0020780 A1 | 1/2005 | Inger et al. | |

(Continued)

FOREIGN PATENT DOCUMENTS

AU 2002221743 B2 5/2002

(Continued)

OTHER PUBLICATIONS

International Search Report mailed May 27, 2008 for PCT Application No. PCT/JP2008/053790 filed Mar. 3, 2008, 8 pages.

(Continued)

*Primary Examiner* — Randy Gulakowski
*Assistant Examiner* — Kara Boyle
(74) *Attorney, Agent, or Firm* — Morrison & Foerster LLP

(57) ABSTRACT

To provide a water absorbing agent which is excellent in balance between absorbency and liquid permeability against pressure and is excellent in flowability at the time of moisture absorption. The water absorbing agent comprises water absorbent resin particles and an organic surface additive, wherein: the organic surface additive having (i) a reactive group for a functional group of a surface of each water absorbent resin particle and (ii) a hydrophobic group exists on the surface of the water absorbent resin particle, and the hydrophobic group has a hydrocarbon group whose carbon number is 8 or more, and a ratio of an oxyalkylene group in a molecular mass of the organic surface additive is 0 or more and 25 mass % or less.

24 Claims, 3 Drawing Sheets

U.S. PATENT DOCUMENTS

| | | |
|---|---|---|
| 2005/0070671 A1* | 3/2005 | Torii et al. .................. 525/329.7 |
| 2005/0113252 A1 | 5/2005 | Miyake et al. |
| 2006/0073969 A1 | 4/2006 | Torii et al. |
| 2006/0204755 A1 | 9/2006 | Torii et al. |

FOREIGN PATENT DOCUMENTS

| | | |
|---|---|---|
| CA | 2426802 A1 | 4/2003 |
| CN | 1216927 A | 5/1999 |
| EP | 1152024 A1 | 11/2001 |
| JP | 61-293246 | 12/1986 |
| JP | 62-149335 | 7/1987 |
| JP | 62-149336 | 7/1987 |
| JP | 3169133 | 7/1991 |
| JP | 05-156034 | 6/1993 |
| JP | 08-092454 | 4/1996 |
| JP | 09-136966 | 5/1997 |
| JP | 2000-198858 | 7/2000 |
| JP | 2001-246835 | 9/2001 |
| JP | 2002-226599 | 8/2002 |
| JP | 2003-511489 B2 | 3/2003 |
| JP | 2003-527213 | 9/2003 |
| JP | 2004-261797 | 9/2004 |
| JP | 2005-097604 | 4/2005 |
| WO | WO-97/37695 A1 | 10/1997 |
| WO | WO-00/10619 A1 | 3/2000 |
| WO | WO-01/74913 A1 | 10/2001 |
| WO | WO-02/34384 A2 | 5/2002 |
| WO | WO-2004-069915 A2 | 8/2004 |

OTHER PUBLICATIONS

Office Action received for Chinese Patent Application No. 200880014575.1, mailed on Jun. 15, 2011, 23 pages (14 pages of English Translation and 9 pages of Office Action).

* cited by examiner

WATER-ABSORBING AGENT AND PRODUCTION METHOD THEREOF

This Nonprovisional application claims priority under U.S.C. §119(a) on Patent Application No. 54855/2007 filed in Japan on Mar. 5, 2007, Patent Application No. 256635/2007 filed in Japan on Sep. 28, 2007, and Patent Application No. 254149/2007 filed in Japan on Sep. 28, 2007, the entire contents of which are hereby incorporated by reference.

FIELD OF THE INVENTION

The present invention relates to a water absorbing agent and a production method thereof. Particularly, the present invention relates to (i) a water absorbing agent which can be favorably used in sanitary materials such as a disposable diaper, a sanitary napkin, a so-called incontinence pad, and the like, and (ii) a production method of the water absorbing agent.

BACKGROUND OF THE INVENTION

An absorbent core (water absorbent core) containing a hydrophilic fiber such as pulp and a water absorbing agent as its components is widely used in sanitary materials such as disposable diapers, sanitary napkins, incontinence pads and the like, in order to absorb body fluids. The absorbent core is used to allow the sanitary material such as the disposable diaper, the sanitary napkin, the incontinence pad, and the like to absorb body fluids.

Recently, these sanitary materials are required to have thinner sizes to realize higher convenience. Thus, smaller amount of a hydrophilic fiber whose bulk density is low and a larger amount of a water absorbing agent having a superior water absorbing property and high bulk density are included in the absorbent core so that a ratio of the hydrophilic fiber is decreased and a ratio of the water absorbent resin is decreased. The ratio of the water absorbing agent contained in the absorbent core is increased in this manner, thereby making the sanitary material thinner without dropping properties such as a water absorption capacity.

However, the sanitary material which includes a smaller amount of the hydrophilic fiber and a larger amount of the water absorbing agent is preferable merely in terms of liquid storage, but raises problems in terms of distribution and diffusion of liquid in actual use in diapers or the like. For example, when a large amount of the water absorbing agent is used, the water absorbing agent becomes soft and gelatinous upon absorbing water. This causes a gel blocking phenomenon which prevents liquid from being absorbed in the water absorbing agent. As a result, a liquid diffusing property of the diaper significantly drops. In order to avoid such phenomenon and to keep high absorbing property of the absorbent core, a ratio of the hydrophilic fiber and the water absorbing agent is inevitably limited, so that there is a limit in making the sanitary material thinner.

In order to achieve a sufficient water absorption capacity while preventing the gel blocking, it is necessary to obtain a water absorbing agent which is excellent in balance between an absorbency represented by centrifugal retention capacity (CRC) or the like and liquid permeability represented by saline flow conductivity (SFC) or the like. However, the relation between the two properties is such that the one drops when the other is enhanced. Thus, it is difficult to enhance the relation therebetween up to a sufficient level. As related means, the following techniques are known for example.

Patent Document 1 discloses a water absorbent resin obtained by treatment with trivalent or further polyvalent cation. Patent Document 2 discloses a technique using an electrostatic or three-dimensional spacer with respect to a water absorbent resin. Patent Document 3 discloses a particulate water absorbing agent including (i) water absorbent resin particles obtained by cross-linking surfaces of irregularly-pulverized particles obtained by cross-linking a monomer containing acrylic acid and/or salt thereof and (ii) a liquid permeability improving agent in order to provide a water absorbing agent having both capillary suction and liquid permeability.

Each of the techniques disclosed in Patent Documents 1 to 3 is such that an additive for improving liquid permeability, e.g., a polyvalent metal salt (metal cation), inorganic particles, polycation, and the like, is added to the water absorbent resin so as to improve the relation between the absorbency and the liquid permeability. But this technique fails to realize the favorable relation (balance). Thus, such technique has been required to be further improved.

Further, the water absorbing agent including the water absorbent resin particles as a main component has a moisture absorbing property, so that its fluidity significantly drops under high humidity. This raises such problem that the workability drops and a similar problem. As means for improving the problem, the following techniques are known.

Patent Document 4 discloses an anti-caking composition including (a) water-insoluble polymer particles which absorb water and are slightly cross-linked, (b) an effective amount of anti-caking agent, and (c) a hydrophobic dust controlling agent of 100 ppm to 6000 ppm relative to a weight of the polymer particles.

As sanitary material water absorbent resin particles whose absorption rate and moisture absorption blocking property are improved, Patent Document 5 discloses modified sanitary material water absorbent resin particles which are a cross-linked polymer of an ethylenic unsaturated monomer having acrylic acid and/or salt thereof as a main component and which have been treated with organic polysiloxane in a liquid state at room temperature.

As water absorbent resin particles whose absorption rate, moisture absorption blocking property, and dust generating property are improved, Patent Document 6 discloses modified water absorbent resin particles obtained by treating particles of a water absorbent resin with a silicone surfactant.

Patent Document 7 discloses a particle material composition which contains inorganic powder (kaoline clay) blended with high water absorbent polymer particles and which is characterized in that less than about 60 mass % of the polymer particles pass through a U.S. standard 50 mesh sieve (300 μm in mesh size).

Patent Document 8 discloses a swelling polymer which is coated with nonionic nitrous surfactant and, as desired, Lewis acid, and which is heat-treated.

However, the foregoing conventional techniques fail to provide a water absorbing agent which satisfactorily achieves various properties.

Further, Patent Document 9 discloses a water absorbent resin which is cross-linked by a polyhydroxy compound and which is coated with or bonds to a nonionic surfactant whose HLB ranges from 3 to 10.

Further, Patent Document 10 discloses a super-absorbent material to which a surfactant has been applied and has permanent wettability.

Further, Patent Document 11 discloses an arrangement in which a surfactant aqueous solution or a surfactant aqueous dispersion liquid is sprayed onto hydrogel formation polymer so as to give specific properties.

Also the techniques disclosed in Patent Documents 9 to 11 fail to realize the favorable relation (balance), so that these techniques are required to be further improved.

[Patent Document 1]
International Publication No. 2001/74913 pamphlet (Publication date: Oct. 11, 2001)

[Patent Document 2]
U.S. Patent application No. 2002/0128618, (Publication date: Sep. 12, 2002)

[Patent Document 3]
International Publication No. 2004/069915 pamphlet (Publication date: Aug. 19, 2004)

[Patent Document 4]
International Publication No. 97/037695 pamphlet (Publication date: Oct. 16, 1997)

[Patent Document 5]
Japanese Patent No. 3169133, (Publication date: May 21, 2001)

[Patent Document 6]
Japanese Unexamined Patent Publication No. 136966/1997 (Tokukaihei 9-136966) (Publication date: May 27, 1997)

[Patent Document 7]
International Publication No. 2000/010619 pamphlet (Publication Date: Mar. 2, 2003)

[Patent Document 8]
International Publication No. 2002/034384 pamphlet (Publication date: May 2, 2002)

[Patent Document 9]
Japanese Unexamined Patent Publication No. 156034/1993 (Tokukaihei 5-156034) (Publication date: Jun. 22, 1993)

[Patent Document 10]
Japanese Translation of PCT International Application No. 527213/2003 (Tokuhyo 2003-527213) (Publication date: Sep. 16, 2003)

[Patent Document 11]
Japanese Translation of PCT International Application No. 511489/2003 (Tokuhyo 2003-511489) (Publication date: Mar. 25, 2003)

SUMMARY OF THE INVENTION

In practically using a water absorbing agent, the water absorbing agent is required to have favorable values of properties such as centrifugal retention capacity, saline flow conductivity, low blocking ratio, and the like, but the foregoing conventional techniques fail to realize the favorable properties. This partially results from the following condition: As to the centrifugal retention capacity and the saline flow conductivity which are important properties of the water absorbing agent, the one drops when the other is enhanced, so that it is difficult to realize both the properties.

The present invention was made in view of the foregoing conventional problems, and an object of the present invention is to provide (i) a water absorbing agent which is excellent in balance between the centrifugal retention capacity and the saline flow conductivity and whose blocking ratio is low and (ii) a production method thereof.

In order to solve the foregoing problems, a water absorbing agent according to the present invention comprises water absorbent resin particles, wherein a compound having (i) a reactive group for a functional group of a surface of each water absorbent resin particle and (ii) a hydrophobic group exists on the surface of the water absorbent resin particle, and the hydrophobic group has a hydrocarbon group whose carbon number is 8 or more, and the compound is represented by the following expression, $13 \leq$ (an average carbon number of the hydrocarbon group whose carbon number is 8 or more+the number of primary to tertiary amine nitrogen atoms)$\leq 26$ where the number of the primary to tertiary amine nitrogen atoms$\geq 0$, a ratio of an oxyalkylene group in a molecular mass of the compound is 0 mass % or more and 25 mass % or less, and at least part of the reactive group bonds to the functional group of the surface of the water absorbent resin particle and/or bonds to the functional group at the time of water absorption.

It is preferable to arrange the water absorbing agent according to the present invention so that the compound is represented by the following expression, $16 \leq$ (an average carbon number of the hydrocarbon group whose carbon number is 8 or more+the number of primary to tertiary amine nitrogen atoms)$\leq 24$ where the number of the primary to tertiary amine nitrogen atoms$\geq 0$.

It is preferable to arrange the water absorbing agent according to the present invention so that at least part of the reactive group has an ionic bound to the surface of the water absorbent resin particle and/or forms an ionic bound to the surface of the water absorbent resin particle at the time of water absorption.

It is preferable to arrange the water absorbing agent according to the present invention so that the water absorbent resin particles and the compound or a solution of the compound or a dispersion liquid of the compound are blended at a temperature lower than 100° C. and are kept at a temperature lower than 100° C.

It is preferable to arrange the water absorbing agent according to the present invention so that the functional group of the surface of the water absorbent resin particle is a carboxyl group.

It is preferable to arrange the water absorbing agent according to the present invention so that the compound is at least one selected from primary amine, secondary amine, and tertiary amine.

It is preferable to arrange the water absorbing agent so that the ionic bond is formed by (i) the compound which is at least one selected from primary amine, secondary amine, and tertiary amine and (ii) the carboxyl group of the surface of the water absorbent resin particle.

It is preferable to arrange the water absorbing agent according to the present invention so that the compound includes a hydrocarbon group whose carbon number is 8 or more and an average carbon number of the hydrocarbon group is 13 to 26.

It is preferable to arrange the water absorbing agent according to the present invention so that the compound is aliphatic amine, and it is more preferable that the compound is alkylamine.

It is preferable to arrange the water absorbing agent according to the present invention so that at least part of the reactive group covalently bonds to the surface of the water absorbent resin particle, and the hydrophobic group has a hydrocarbon group whose carbon number is 8 or more, and an average carbon number of the hydrocarbon group is 14 or more.

It is preferable to arrange the water absorbing agent according to the present invention so that a rate of a reaction of the compound to the water absorbent resin particles is 10% or more and less than 100%.

It is preferable to arrange the water absorbing agent according to the present invention so that 0.001 mass % or more and less than 1 mass % of the compound relative to the water absorbing agent is extracted by rinsing the water absorbing agent with ethanol.

It is preferable to arrange the water absorbing agent according to the present invention so that the compound has at least two hydroxyl groups in case where the compound has each hydroxyl group as the reactive group.

It is preferable to arrange the water absorbing agent according to the present invention so that: in case where the compound has a nitrogen atom, the compound has at least one reactive group and has a hydrophobic group having a hydrocarbon group which bonds to the nitrogen atom and whose average carbon number is 14 or more.

It is preferable to arrange the water absorbing agent according to the present invention so that the compound is at least one kind selected from aliphatic esterified nonionic surfactants.

It is preferable to arrange the water absorbing agent according to the present invention so that the compound is at least one kind selected from aliphatic amine, cationic surfactant, and amphoteric surfactant.

It is preferable to arrange the water absorbing agent according to the present invention so that a mass average particle diameter is 100 μm or more and 600 μm or less and a ratio of particles whose particle diameter is less than 150 μm is 5 mass % or less.

It is preferable to arrange the water absorbing agent according to the present invention so that the surface of the water absorbent resin particle is cross-linked.

It is preferable to arrange the water absorbing agent according to the present invention so that an amount of the compound relative to an entire amount of the water absorbing agent is 0.001 mass % or more and 5 mass % or less.

In order to solve the foregoing problems, a method according to the present invention for producing a water absorbing agent including water absorbent resin particles, said method comprises the mixing step in which the water absorbent resin particles are mixed with a compound having (i) a reactive group for a functional group of a surface of each water absorbent resin particle and (ii) a hydrophobic group, wherein the hydrophobic group has a hydrocarbon group whose carbon number is 8 or more, and the compound is represented by the following expression, $$13 \leq (\text{an average carbon number of the hydrocarbon group whose carbon number is 8 or more} + \text{the number of primary to tertiary amine nitrogen atoms}) \leq 26,$$

where the number of the primary to tertiary amine nitrogen atoms $\geq 0$, a ratio of an oxyalkylene group in a molecular mass of the compound is 0 or more and 25 mass % or less.

It is preferable to arrange the method according to the present invention so that at least part of the reactive group has an ionic bound to the functional group of the surface of the water absorbent resin particle and/or forms an ionic bond to the functional group at the time of water absorption, and the mixing step is carried out at a temperature lower than 100° C., and the water absorbing agent is kept at a temperature lower than 100° C. after the mixing step.

It is preferable to arrange the method according to the present invention so as to further comprise the mixing step is carried out after a surface cross-linking step in which the vicinity of the surface of the water absorbent resin particle is cross-linked with a surface cross-linking agent.

It is preferable to arrange the method according to the present invention so that the compound is mixed in a solution or a dispersion liquid.

It is preferable to arrange the method according to the present invention so that: as said compound, a compound in which at least part of the reactive group has a covalent bond to the surface of the water absorbent resin particle is used, and the water absorbent resin particles and the compound are mixed before and/or during the surface cross-linking, and a temperature at the time of the cross-linking reaction is 120° C. or higher and 240° C. or lower.

It is preferable to arrange the method according to the present invention so that a polyhydric alcohol which is not equivalent to the compound is mixed at the time of the cross-linking reaction.

In order to solve the foregoing problems, an absorbent core according to the present invention comprises the aforementioned water absorbing agent.

According to the present invention, it is possible to provide (i) a water absorbing agent which is excellent in balance between centrifugal retention capacity (CRC) and saline flow conductivity (SFC) and which has a low blocking ratio and (ii) a production method thereof. Further, preferably, according to the present invention, by obtaining a water absorbing agent which is excellent in balance between centrifugal retention capacity (CRC) indicative of an absorption capacity of the water absorbing agent and saline flow conductivity (SFC) indicative of liquid permeability, it is possible to provide an absorbent core including the water absorbing agent which is excellent in water absorption rate.

Additional objects, features, and strengths of the present invention will be made clear by the description below. Further, the advantages of the present invention will be evident from the following explanation in reference to the drawings.

DESCRIPTION OF THE EMBODIMENTS

Figure 1:
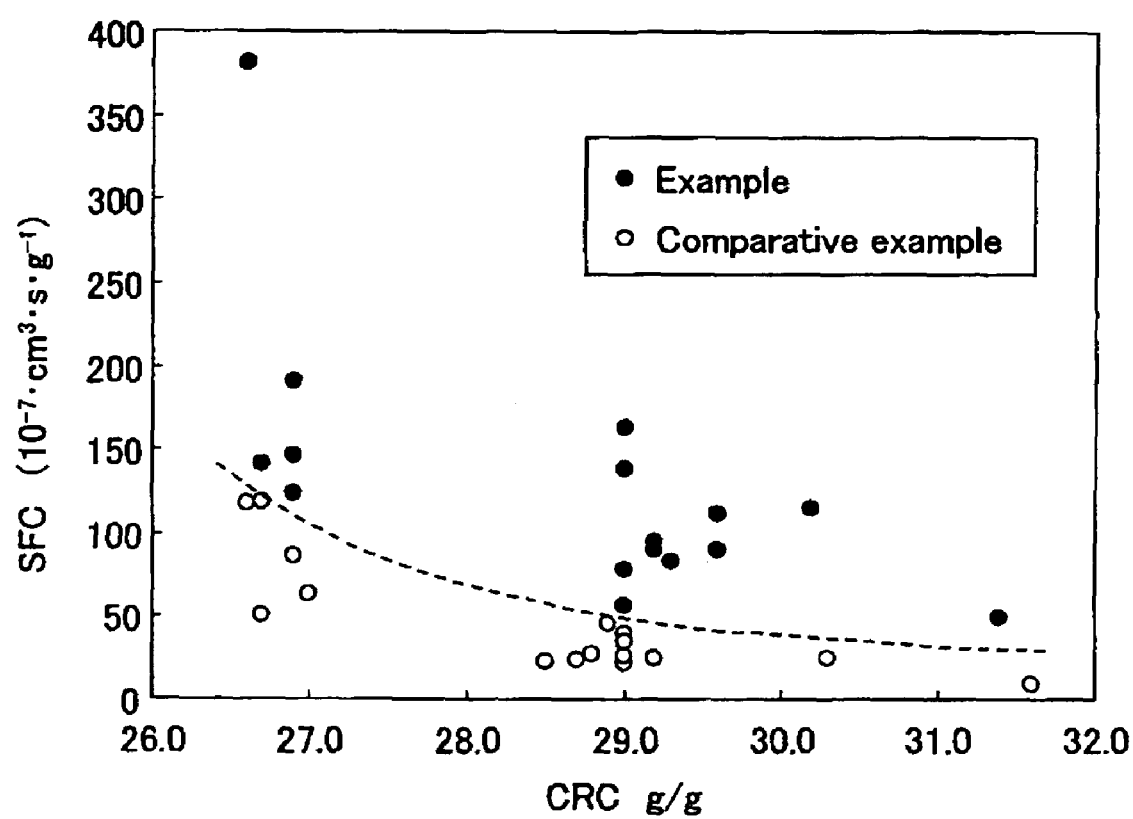
FIG. 1 is a graph illustrating a relation between SFC and CRC of a water absorbing agent obtained in each of Examples and Comparative Examples.

The following description will detail the present invention. However, the scope of the present invention is not limited to the embodiment, but may be altered without departure from the spirit and effect of the present invention. Note that, in the present specification, "mass" is a synonymous of "weight". Further, "mass %" is synonymous of "weight %". In the description, "mass" and "mass %" are exclusively used.

First, terms in the description are defined as follows. In the present, specification, CRC represents centrifugal retention capacity and refers to a value obtained by a measurement method described in Examples later. Further, SFC represents saline flow conductivity and refers to a value obtained by a measurement method described in Examples later. Further, AAP represents absorbency against pressure of 4.83 kPa and refers to a value obtained by a measurement method described in Examples later. Further, D50 (distribution) represents a mass average particle diameter and refers to a value obtained by a measurement method described in Examples later. Further, σζ is a particle diameter distribution logarithmic standard deviation and refers to a value obtained by a measurement method described in Examples later. Further, BR represents a blocking ratio and refers to a value obtained by a measurement method described in Examples later. Further, in the present specification, a physiological saline is a sodium chloride aqueous solution (0.9 mass %).

The water absorbing agent according to the present invention includes water absorbent resin particles and further includes a compound having (i) a reactive group for a functional group of a surface of each water absorbent resin particle and (ii) a hydrophobic group.

In the present invention, the water absorbing agent means an absorbing and solidifying agent of aqueous liquid which agent includes water absorbent resin particles as a main component and further includes a compound having (i) a reactive group for a functional group of a surface of each water absorbent resin particle and (ii) a hydrophobic group (hereinafter, the "compound" is sometimes referred to as "organic surface additive" in the present specification), and which agent contains a small amount of additive and/or water as necessary. Herein, the "main component" means that an amount of the water absorbent resin particles is 50 mass % or more relative to an entire amount of the water absorbing agent. The amount of the water absorbent resin particles is more preferably 60 mass % or more and 99.999 mass % or less, still more preferably 80 mass % or more and 99.999 mass % or less, still further more preferably 90 mass % or more and 99.999 mass % or less, particularly preferably 95 mass % or more and 99.999 mass % or less, most preferably 98 mass % or more and 99.999 mass % or less, relative to the entire amount of the water absorbing agent.

Further, an amount of the compound having (i) a reactive group for a functional group of a surface of each water absorbent resin particle and (ii) a hydrophobic group is preferably 0.001 mass % or more and 20 mass % or less, more preferably 0.005 mass % or more and 10 mass % or less, still more preferably 0.01 mass % or more and 10 mass % or less, still further more preferably 0.05 mass % or more and 5 mass % or less, particularly preferably 0.1 mass % or more and 2 mass % or less, most preferably 0.1 mass % or more and 1 mass % or less.

As a component other than the water absorbent resin particles and the compound (the organic surface additive) of the water absorbing agent according to the present invention, water is generally used as a main component, and a small amount of other additive is used as necessary.

Note that, the water absorbing agent is an absorbing and solidifying agent of aqueous liquid, but the aqueous liquid is not limited to water and may be urine, blood, feces, waste fluid, moisture, vapor, ice, a mixture of water and organic solvent and/or inorganic solvent, rain water, ground water, and the like, as long as the aqueous liquid includes water. It is preferable that the water absorbing agent is an absorbing and solidifying agent which absorbs and solidifies urine, particularly human urine, out of the aforementioned aqueous liquids.

The following will explain (1) Water absorbent resin particles included in the water absorbing agent of the present invention, (2) Compound (organic surface additive) having (i) a reactive group for a functional group of a surface of each water absorbent resin particle and (ii) a hydrophobic group, (3) Production method of the water absorbing agent, (4) Water absorbing agent, and (5) Absorbent core, in this order.

(1) Water Absorbent Resin Particles Included in the Water Absorbing Agent of the Present Invention The water absorbent resin particles used in the water absorbing agent according to the present invention are particles of water-insoluble water-swelling hydrogel formation polymer obtained by polymerizing a water-insoluble unsaturated monomer (hereinafter, the water absorbent resin is sometimes referred to as the water-insoluble water-swelling hydrogel formation polymer).

Specific examples of the water-insoluble water-swelling hydrogel formation polymer include: a partially neutralized cross-linked polyacrylic acid polymer (U.S. Pat. No. 4,625,001, U.S. Pat. No. 4,654,039, U.S. Pat. No. 5,250,640, U.S. Pat. No. 5,275,773, European Patent No. 456136, and the like); a cross-linked partially neutralized starch-acrylic acid graft polymer (U.S. Pat. No. 4,076,663); an isobutylene-maleic acid copolymer (U.S. Pat. No. 4,389,513); a saponified vinyl acetate-acrylic acid copolymer (U.S. Pat. No. 4,124,748); a hydrolyzed acrylamide (co)polymer (U.S. Pat. No. 3,959,569); a hydrolyzed acrylonitrile copolymer (U.S. Pat. No. 3,935,099); and the like.

It is more preferable that the water absorbent resin particles included in the water absorbing agent of the present invention are particles of water absorbent resin made of polyacrylic acid (salt) cross-linked polymer obtained by polymerizing a monomer containing acrylic acid and/or salt thereof as the water-insoluble unsaturated monomer. Herein, the polyacrylic acid (salt) cross-linked polymer is a cross-linked polymer obtained by polymerizing a monomer containing 50 mol % or more, preferably 70 mol % or more, more preferably 90 mol % or more of acrylic acid and/or salt thereof.

Further, preferably 50 mol % or more and 90 mol % or less, more preferably 60 mol % or more and 80 mol % or less of acid group of the polyacrylic acid (salt) cross-linked polymer is neutralized. Further, examples of polyacrylic acid salt include alkali metal salt such as sodium, potassium, and lithium; ammonium salt; amine salt; and the like. Above all, it is more preferable that polyacrylic acid salt is sodium salt. The acid group for forming salt may be neutralized in a monomer phase before the polymerization or in a polymer phase during or after the polymerization, or the neutralization may be carried out in both or all the phases.

As to the polyacrylic acid (salt) cross-linked polymer favorably used in the present invention as the water absorbent resin particles, not only the unsaturated monomer (acrylic acid and/or salt thereof) used as a main component but also other monomer may be copolymerized as necessary.

Specific examples of other monomer include: anionic unsaturated monomer such as methacrylic acid, maleic acid, vinyl sulfonic acid, styrene sulfonic acid, 2-(meth)acrylamide-2-methylpropane sulfonic acid, 2-(meth)acryloyl ethane sulfonic acid, 2-(meth)acryloyl propane sulfonic acid, and salt thereof; nonionic hydrophilic unsaturated monomer such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl(meth)acrylate, methoxypolyethyleneglycol(meth)acrylate, polyethyleneglycolmono(meth)acrylate, vinylpyridine, N-vinylpyrrolidone, N-acryloylpiperidine, N-acryloylpyrrolidine, and N-vinylacetamide; cationic unsaturated monomer such as N,N-dimethylaminoethyl(meth)acrylate, N,N-diethylaminoethyl(meth)acrylate, N,N-dimethylaminopropyl(meth)acrylate, N,N-dimethylaminopropyl(meth)acrylamide and quaternary salt thereof; and the like. An amount of the monomer other than the acrylic acid and/or salt thereof is preferably 0 mol % or more and 30 mol % or less, more preferably 0 mol % or more and 10 mol % or less, relative to the whole monomer.

The water absorbent resin particles usable in the present invention is a cross-linked polymer having an internal cross-linked structure. As to a method for introducing the internal cross-linked structure into the water absorbent resin particles used in the present invention, examples thereof include: a method in which self-cross-linking is carried out without using any cross-linking agent so as to introduce the internal cross-linked structure; a method in which an internal cross-linking agent having two or more polymerizable unsaturated groups in its molecule and/or two or more reactive groups in its molecule is copolymerized or reacted so as to introduce the internal cross-linked structure; and a similar method. Above all, it is more preferable to adopt the method in which the internal cross-linking agent is copolymerized or reacted.

Specific examples of the internal cross-linking agent include: N,N'-methylenebis(meth)acrylamide, (poly)ethyleneglycol di(meth)acrylate, (poly)propyleneglycol di(meth)acrylate, trimethylolpropanetri(meth)acrylate, trimethylolpropanedi(meth)acrylate, glycerintri(meth)acrylate, glycerinacrylatemethacrylate, ethylene oxide denatured trimethylolpropanetri(meth)acrylate, pentaerythritoltetra(meth)acrylate, dipentaerythritolhexa(meth)acrylate, triallyl cyanurate, triallyl isocyanurate, triallyl phosphate, triallyl amine, poly(meth)allyloxyalkane, (poly)ethyleneglycoldiglycidylether, and glyceroldiglycidylether; polyhydric alcohols such as ethyleneglycol, polyethyleneglycol, 1,4-butanediol, propyleneglycol, glycerin, and pentaerythritol; ethylenediamine, polethyleneimine, glycidyl(meth)acrylate, and the like.

These internal cross-linking agents may be used independently or in a combination of two or more kinds. In view of absorbing properties of the resultant water absorbent resin particles, it is preferable to essentially use a compound having two or more polymerizable unsaturated groups as the internal cross-linking agent.

An amount of the internal cross-linking agent is preferably 0.005 mol % or more and 3 mol % or less, more preferably 0.01 mol % or more and 1.5 mol % or less, most preferably 0.05 mol % or more and 0.2 mol % or less, relative to the whole monomer.

In carrying out the polymerization, it is possible to add hydrophilic polymers such as a mixture of starch and cellulose, a derivative of starch and cellulose, polyvinyl alcohol, polyacrylic acid (salt), cross-linked polyacrylic acid (salt), and the like or it is possible to add a chain transfer agent such as hypophosphorous acid (salt).

Further, in polymerizing the monomer containing acrylic acid and/or salt thereof as a main component, it is preferable to carry out bulk polymerization, reversed phase suspension polymerization, or precipitation polymerization. However, in terms of (i) performance of the water absorbent resin particles and (ii) controllability of polymerization, a more preferable method of polymerization is aqueous solution polymerization performed under such condition that an aqueous solution of the monomer is used. Such polymerization method is recited for example in U.S. Pat. No. 4,625,001, U.S. Pat. No. 4,769,427, U.S. Pat. No. 4,873,299, U.S. Pat. No. 4,093,776, U.S. Pat. No. 4,367,323, U.S. Pat. No. 4,446,261, U.S. Pat. No. 4,683,274, U.S. Pat. No. 4,690,996, U.S. Pat. No. 4,721,647, U.S. Pat. No. 4,738,867, U.S. Pat. No. 4,748,076, U.S. Patent Publication No. 2002/40095.

In carrying out the polymerization, it is possible to use: a radical polymerization initiator such as potassium persulfate, ammonium persulfate, sodium persulfate, t-butylhydroperoxide, hydrogen peroxide, 2,2'-azobis (2-amidino-propane) dihydrochloride; or an active energy ray such as an ultraviolet ray and an electron ray. Further, in case of using a radical polymerization initiator, redox polymerization may be carried out by using a reducer such as sodium sulfite, sodium bisulfite, ferrous sulfate, L-ascorbic acid, and the like, together. An amount of polymerization initiators used is preferably 0.001 mol % or more and 2 mol % or less, more preferably 0.01 mol % or more and 0.5 mol % or less, relative to the whole monomer.

A shape of the water absorbent resin particles obtained by the foregoing polymerization is generally an irregularly-pulverized shape, a spherical shape, a fibrous shape, a bar shape, a substantially spherical shape, an oblate shape, and the like. It is more preferable that the shape is the irregularly-pulverized shape. If the water absorbent resin particles have the irregularly-pulverized shape, the below-described compound (organic surface additive) having (i) a reactive group for a surface of each water absorbent resin particle and (ii) a hydrophobic group can be made more efficiently exist on the surface of the water absorbent resin particle.

In case where the cross-linked polymer is obtained by the aqueous solution polymerization and is in a gelatinous state, that is, in case of cross-linked polymer hydrogel (hereinafter, the cross-linked polymer hydrogel is sometimes referred to as "hydrogel" in the present specification), the cross-linked polymer hydrogel is dried and is generally pulverized before and/or after the drying so as to obtain water absorbent resin particles. Note that, in the present invention, "drying" means an operation for increasing a solid content. Generally, the drying operation may be carried out in any manner as long as the solid content is increased compared with that which has not been subjected to the drying operation, but it is preferable that: the solid content is 85 mass % or more, preferably 90 mass % or more, and its upper limit is about 99 mass %. The drying may be carried out at the same time as the polymerization, and the drying at the time of the polymerization and the drying after the polymerization may be carried out in combination, but it is more preferable to carry out the drying step using a dryer after the polymerization. In the present invention, the solid content of the water absorbent resin after being dried is preferably 90 mass % or more, more preferably 95 mass % or more. If the solid content is smaller, the fluidity drops, which causes a trouble in the production and also prevents the water absorbent resin from being pulverized, so that it may be impossible to control the particle distribution within a specific range. Note that, the solid content of the water absorbent resin refers to a value measured by the below-described measurement method.

In the present invention, the drying is carried out at a temperature ranging from 100° C. to 250° C. during a period equal to or longer than 50% of the entire drying step, more preferably throughout the drying step. At a temperature lower than 100° C., an internal polymer chain of the water absorbent resin less changes, which results in less internal cross-linking effect, so that it may be impossible to improve properties thereof. Further, at the temperature lower than 100° C., it takes time to complete the drying. As a result, a large amount of undried product occurs, so that this causes a trouble in steps such as the pulverization. Further, if the drying is carried out at 250° C. or higher, the water absorbent resin is damaged, which results in increase of an extractable polymer content, so that it may be impossible to improve the properties thereof. Note that, the drying temperature is defined by a heat medium temperature. However, if it is impossible to define the drying temperature by a temperature of a heat medium such as microwave, the drying temperature is defined by a material temperature. The drying method is not particularly limited as long as the drying temperature is within a temperature ranging from 100° C. to 250° C. It is possible to favorably adopt hot-air drying, airless drying, reduced-pressure drying, infrared drying, microwave drying. Above all, it is more preferable to adopt the hot-air drying. A hot airflow in the hot-air drying is preferably 0.01 to 10 m/sec, more preferably 0.1 to 5 m/sec.

The drying temperature more preferably ranges from 130° C. to 220° C., more preferably 150° C. to 200° C. Further, the drying may be carried out at a constant temperature or the drying temperature may be varied, but it is preferable that substantially the entire drying step is carried out within the foregoing temperature range.

A drying time depends on a polymer surface area, a moisture content, and a type of a dryer, and is suitably set so as to achieve the desired moisture content. The drying time generally ranges from 10 to 120 minutes, more preferably 20 to 90 minutes, still more preferably 30 to 60 minutes. If the drying time is less than 10 minutes, an internal polymer chain of the water absorbent resin less changes, which results in less internal cross-linking effect, so that it may be impossible to improve the properties thereof. Further, if the drying time is less than 10 minutes, a large amount of undried product occurs, which may cause a trouble in the pulverization. Further, if the drying time is 120 minutes or longer, the water absorbent resin may be damaged, which results in increase of the extractable polymer content, so that it may be impossible to improve the properties thereof.

The water absorbent resin obtained by the method for producing water absorbent resin particles is pulverized by a pulverizer. The pulverization may be carried out before, during, or after the drying, but it is preferable to carry out the pulverization after the drying. The pulverizer is not particularly limited, but for example, a rolling pulverizer such as a roll mill, a hammering pulverizer such as a hammer mill, an impact pulverizer, a cutter mill, turbo grinder, a ball mill, a flash mill, and the like may be used. Above all, the roll mill is preferable in controlling the particle diameter distribution. In order to control the particle diameter distribution, the pulverization may be carried out twice or more times continuously, preferably three or more times continuously. In case of carrying out the pulverization twice or more times, a single pulverizer may be used or respective pulverizers may be used. Further, also a combination of different types of pulverizers may be used.

In order to control the particle diameter distribution of the thus pulverized water absorbent resin particles into a specific particle diameter distribution, the particles may be classified by a sieve having a specific mesh size. A classifier used to classify the particles with a sieve is not particularly limited, but examples thereof include: a vibrating sieve (unbalance-weight driving type, resonance type, vibrating motor type, electromagnetic type, circular vibrating type, or the like); an in-surface moving sieve (horizontal movement type, horizontal circular-linear movement type, three-dimensional movement type, and the like); a movable screen sieve; a forced-stirring type sieve; a screen-face vibrating type sieve; a pneumatic sieve; a sonic wave sieve; and the like. It is more preferable to use the vibrating sieve and the in-surface moving sieve. Further, the mesh size of the sieve is preferably 1000 μm to 300 μm, more preferably 900 μm to 400 μm, still more preferably 710 μm to 450 μm. If the mesh size is out of these ranges, it may be impossible to obtain the desired particle diameter distribution.

In order to control the particle diameter distribution of the water absorbent resin particles classified in the foregoing manner into a specific range, further classification may be carried out so as to partially or entirely remove particles whose particle diameter is less than the specific particle diameter. A classifier used in this step is not particularly limited, but the above-mentioned sieves are favorably used. Besides, a fine-powder classification device (a centrifugal type, an inertial type, and the like) or a similar device may be used. Also in the present step, particles whose particle diameter is preferably less than 200 μm, more preferably less than 150 μm, most preferably less than 106 μm are partially or entirely removed.

It is more preferable that the vicinity of a surface of each water absorbent resin particle used in the present invention is cross-linked with an organic cross-linking agent and/or a water-soluble inorganic cross-linking agent serving as the surface cross-linking agent. In this manner, the vicinity of the surface of the water absorbent resin particle included in the water absorbing agent is cross-linked, which makes it possible to reduce a re-wet amount in exerting a pressure onto a swollen water absorbing agent. Thus, it is possible to improve AAP, in other words, absorbency against pressure.

The surface of the water absorbent resin particle may be cross-linked with the surface cross-linking agent at any stage, but it is preferable to carry out the surface cross-linking after carrying out the operation for controlling the particle diameter distribution of the water absorbent resin particles into a specific range. Further, an example of a preferred addition method is a method in which the below-described compound (organic surface additive) having (i) a reactive group for a functional group of a surface of each water absorbent resin particle and (ii) a hydrophobic group is included in a solution of the surface cross-linking agent so as to be added.

An example of the surface cross-linking agent usable in the surface cross-linking treatment is an organic surface cross-linking agent and/or a water-soluble inorganic surface cross-linking agent each of which has two or more functional groups which can react with a functional group of the water absorbent resin particle, e.g., a carboxyl group of the water absorbent resin particle. It is more preferable to use a water-soluble organic surface cross-linking agent.

Examples of the surface cross-linking agent include: polyhydric alcohols such as ethyleneglycol, diethyleneglycol, propyleneglycol, triethyleneglycol, tetraethyleneglycol, polyethyleneglycol, 1,3-propanediol, dipropyleneglycol, 2,2,4-trimethyl-1,3-pentandiol, polypropyleneglycol, glycerin, polyglycerin, 2-butene-1,4-diol, 1,3-butandiol, 1,4-butandiol, 1,5-pentandiol, 1,6-hexanediol, 1,2-cyclohexanedimethanol, 1,2-cyclohexanol, trimethylolpropane, diethanolamine, triethanolamine, polyoxypropylene, oxyethlene-oxypropylene block copolymer, pentaerythritol, and sorbitol; epoxy compounds such as ethyleneglycol diglycidyl ether, polyethyleneglycol diglycidyl ether, glycerol polyglycidyl ether, diglycerol polyglycidyl ether, polyglycerol polyglycidyl ether, propyleneglycol diglycidyl ether, polypropyleneglycol diglycidyl ether, and glycidol; multivalent amine compounds such as ethylenediamine, diethylenetriamine, triethylenetetramine, tetraethylenepentamine, pentaethylenehexamine, and polyethyleneimine, and inorganic salts or organic salts thereof (for example, azetidinium salt and the like); multivalent isocyanate compounds such as 2,4-tolylenediisocyanate and hexamethylenediisocyanate; multivalent oxazoline compounds such as 1,2-ethylenebisoxazoline; carbonic acid derivatives such as urea, thiourea, guanidine, dicyandiamide, and 2-oxazolidinon; alkylene carbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, and 1,3-dioxisopane-2-one; haloepoxy compounds such as epichlorohydrin, epibromohydrin, and α-methylepichlorohydrin, and multivalent amine addition products thereof (for example, Kymene produced by Hercules: registered trademark); silane coupling agents such as γ-glycidoxypropyltrimethoxysilane and γ-aminopropyltriethoxysilane; and oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol, 3-chloromethyl-3-methyloxetane, 3-chloromethyl-3-ethyloxetane, and a multivalent oxetane compound; and the like.

These surface cross-linking agents may be used either independently or in a suitable combination of two or more kinds. Among the cross-linking agents, the polyhydric alcohol is preferable since it is superior in terms of safety and it improves the hydrophilic property of the surface of the water absorbent resin particle.

An amount of the surface cross-linking agent used is preferably 0.001 to 5 parts by mass relative to 100 parts by mass of the solid content of the water absorbent resin particles.

In mixing the surface cross-linking agent with the water absorbent resin particles, water may be used. An amount of water to be used is preferably over 0.5 parts by mass and not more than 10 parts by mass, more preferably 1 part by mass to 5 parts by mass, relative to 100 parts by mass of the solid content of the water absorbent resin particles.

Further, in mixing the surface cross-linking agent or aqueous solution thereof with the water absorbent resin particles, a hydrophilic organic solvent and a third substance may be used as a mixing coadjuvant. In case of using the hydrophilic organic solvent, a hydrophilic solvent described in International Publication No. 2004/069915 can be used for example.

An amount of the hydrophilic organic solvent varies depending on a type, a particle diameter, a moisture content, and the like of the water absorbent resin particles. However, the amount of the hydrophilic organic solvent is preferably 10 parts by mass or less, more preferably 0 part by mass to 5 parts by mass, relative to 100 parts by mass of the solid content of the water absorbent resin particles.

Further, inorganic acid, organic acid, polyamino acid, etc. that are recited in European Patent No. 0668080 as a third substance may exist therein. Such mixing coadjuvant may act as a surface cross-linking agent, but it is preferable to use a substance which prevents a water absorbing performance of the water absorbent resin particles from dropping after performing the surface cross-linking treatment. It is preferable that the water absorbent resin particles used in the present invention are mixed with the surface cross-linking agent having no hydrophilic organic solvent whose boiling point is 100° C. or lower and are heated so as to be cross-linked. In case where the water absorbent resin particles include the hydrophilic organic solvent whose boiling point is 100° C. or lower, a manner in which the surface cross-linking agent exists on the surface of the water absorbent resin particle is varied by evaporation of the hydrophilic organic solvent, so that it may be impossible to sufficiently realize properties such as SFC.

In order to evenly mix the water absorbent resin particles with the surface cross-linking agent, it is preferable that water-soluble inorganic bases (more preferably, persulfate) may coexist in mixing the water absorbent resin particles with the surface cross-linking agent. An amount of the water-soluble organic bases varies depending on a type, a particle diameter, etc. of the water absorbent resin particles, but preferably ranges from 0.01 to 1 parts by mass, more preferably from 0.05 to 5 parts by mass, relative to 100 parts by mass of the solid content of the water absorbent resin particles. That is, it is preferable that, relative to the water absorbent resin particles, 0.01 mass % to 1.0 mass % of the organic surface cross-linking agent and/or water-soluble inorganic surface cross-linking agent containing water-soluble inorganic bases, preferably, persulfate is mixed and the mixture is heated so as to be cross-linked.

The method for mixing the water absorbent resin particles with the hydrophilic organic solvent is not particularly limited, but the following mixing methods may be performed: the water absorbent resin particles are immersed in the hydrophilic organic solvent, and a surface cross-linking agent dissolved in water and/or the hydrophilic organic solvent as required is mixed; the surface cross-linking agent dissolved in the water and/or the hydrophilic solvent is sprayed or dropped directly to the water absorbent resin particles.

Generally, it is preferable that the water absorbent resin particles are subjected to a heat-treatment so as to promote the cross-linking reaction after mixing the water absorbent resin particles with the surface cross-linking agent. Further, in case where the below-described compound (organic surface additive) having (i) a reactive group for a functional group of a surface of each water absorbent resin particle and (ii) a hydrophobic group is added in the surface cross-linking step, it is preferable to carry out the heat-treatment, after mixing the water absorbent resin particles, the surface cross-linking agent, and a specific organic surface additive of the present invention, so as to promote the cross-linking reaction. A heating temperature varies depending on the surface cross-linking agent used, but the heating temperature preferably ranges from 40° C. to 250° C., more preferably from 100° C. to 240° C., still more preferably from 150° C. to 230° C. In case where the heating temperature is less than 40° C., the absorbing property such as AAP and SFC may be insufficiently improved. In case where the heating temperature exceeds 250° C., the water absorbent resin particles deteriorate which causes various performances to drop. A heating time preferably ranges from one minute to two hours, more preferably from five minutes to one hour.

A mass average particle diameter of the water absorbent resin particles used in the present invention is preferably 100 to 600 μm, more preferably 200 to 500 μm, most preferably 300 to 400 μm. When the mass average particle diameter is within the range of 100 to 600 μm, the liquid permeability and liquid diffusing property are remarkably improved or the absorption rate is greatly improved. In case where the water absorbent resin particles are used in a diaper for example, liquid leakage is reduced.

Further, as the water absorbent resin particles used in the present invention, preferably 50 mass % or more, more preferably 80 mass % or more of water absorbent resin particles whose particle diameter is 175 μm or more and 710 μm or less are used.

Further, as to the water absorbent resin particles used in the present invention, a ratio of particles passing through a sieve whose mesh size is 150 μm, that is, a ratio of particles whose particle diameter is less than 150 μm is preferably 5 mass % or less, more preferably 3 mass % or less, still more preferably 1 mass % or less, relative to the entire amount of the water absorbent resin particles. If such water absorbent resin particles that the ratio of particles passing through the sieve whose mesh size is 150 μm is 5 mass % or less relative to the entire amount of the water absorbent resin particles are used in the water absorbing agent, it is possible to suppress an amount of dusts of the resultant water absorbing agent. Thus, it is possible to prevent occurrence of safety and sanitary problems caused by dispersion of fine particles included in the water absorbent resin particles at the time of production of the water absorbing agent. This makes it possible to suppress drop of the properties of the resultant water absorbing agent. Note that, in case where the aforementioned ratio exceeds 5 mass %, dusts are likely to occur at the time of production of the water absorbing agent, and this may result in safety and sanitary problems. Further, in case where the aforementioned ratio exceeds 5 mass %, this may drop properties of the absorbent core.

Further, as the water absorbent resin particles, it is possible to use water absorbent resin particles obtained by agglomerating and drying fine-powdery water absorbent resin particles whose mass average particle diameter is 300 μm or less (hereinafter, referred to as "fine powder") and by adjusting a particle diameter thereof and carrying out surface cross-linking. Further, it is possible to use water absorbent resin particles obtained by partially mixing agglomerated fine powder with water absorbent resin particles, i.e., primary particles obtained by pulverization and having an irregularly-pulverized shape. In case where the agglomerated fine powder is partially mixed with the water absorbent resin particles, it is possible to obtain a water absorbing agent which is more excellent in the absorbent rate, a below-described FHA, and other absorbing properties. An amount of the agglomerated fine powder mixed with the water absorbent resin particles is preferably 5 mass % or more, more preferably 10 mass % or more, still more preferably 15 mass % or more, most preferably 20 mass % or more. Note that, a particle diameter of the fine powder is indicated by a sieve mesh size with which the fine powder is classified.

As a method for producing the agglomerated fine powder, it is possible to adopt a known technique for reproducing fine powder. Examples of the adoptable method include: a method in which a mixture of warm water and the fine powder is dried (U.S. Pat. No. 6,228,930); a method in which a mixture of the fine powder and a monomer aqueous solution is polymerized (U.S. Pat. No. 5,264,495); a method in which water is added to the fine powder and the resultant is agglomerated at a specific surface pressure or higher surface pressure (European Patent No. 844270); a method in which the fine powder is sufficiently swollen into an amorphous gel and the thus formed gel is dried and pulverized (U.S. Pat. No. 4,950,692); a method in which the fine powder and a polymerized gel are mixed (U.S. Pat. No. 5,478,879); and a similar method.

Above all, as the method for producing the agglomerated fine powder, it is preferable to adopt the aforementioned method in which warm water and the fine powder are mixed and the mixture is dried. The water absorbent resin particles agglomerated by this method are preferable since the water absorbent resin particles have a porous structure (which is synonymous with the porous structure described in Japanese Unexamined Patent Publication: Tokukai 2004-261797). The water absorbent resin particles used in the present invention include preferably 5 mass % or more, more preferably 10 mass % or more, still more preferably 15 mass % or more, particularly preferably 20 mass % or more of particles having a porous structure. If the water absorbent resin particles include the agglomerated fine powder having a porous structure, the water absorbent resin particles or the water absorbing agent including the same are excellent in a fixed height absorbency (FHA) described in U.S. Patent Publication No. 2005/0003191A1.

The CRC of the water absorbent resin particles used in the present invention is preferably 5 (g/g) or more, more preferably 15 (g/g) or more, and still more preferably 25 (g/g) or more, particularly preferably 28 (g/g) or more. An upper limit of the CRC is not particularly limited, but the upper limit is preferably 60 (g/g) or less, more preferably 50 (g/g) or less, still more preferably 40 (g/g) or less. In case where the CRC is less than 5 (g/g) and the water absorbent resin particles having such CRC are used in the water absorbing agent, an absorption capacity is too small to be favorably used in a sanitary material such as a diaper. Further, in case where the CRC is more than 50 (g/g) and the water absorbent resin particles having such CRC are used in the water absorbing agent, it may be impossible to obtain the water absorbing agent which is excellent in a rate at which the absorbent core absorbs liquid.

The AAP of the water absorbent resin particles used in the present invention is 8 (g/g) or more, preferably 16 (g/g) or more, more preferably 20 (g/g) or more, still more preferably 22 (g/g) or more, most preferably 24 (g/g) or more. An upper limit of the AAP is not particularly limited, but the upper limit is preferably 30 (g/g) or less. In case where the AAP is less than 8 (g/g) and the water absorbent resin particles having such AAP are used in the water absorbing agent, it may be impossible to obtain the water absorbing agent whose re-wet amount is small when a pressure is exerted onto the water absorbing agent.

The SFC of the water absorbent resin particles used in the present invention is preferably $10(10^{-7} \cdot cm^3 \cdot s \cdot g^{-1})$ or more, more preferably $30(10^{-7} \cdot cm^3 \cdot s \cdot g^{-1})$ or more, still more preferably $50(10^{-7} \cdot cm^3 \cdot s \cdot g^{-1})$ or more, still further more preferably $70(10^{-7} \cdot cm^3 \cdot s \cdot g^{-1})$ or more, particularly preferably $100 (10^{-7} \cdot cm^3 \cdot s \cdot g^{-1})$ or more, most preferably $150(10^{-7} \cdot cm^3 \cdot s \cdot g^{-1})$. In case where the SFC is less than $10(10^{-7} \cdot cm^3 \cdot s \cdot g^{-1})$, the liquid permeability is not improved even though there is included the compound having (i) a reactive group for a functional group of a surface of each water absorbent resin particle and (ii) a hydrophilic group. Thus, it may be impossible to obtain the water absorbing agent excellent in the rate at which the absorbent core absorbs liquid in case where the water absorbent resin particles are used in the water absorbing agent. An upper limit of the SFC is not particularly limited, but the upper limit is preferably $3000(10^{-7} \cdot cm^3 \cdot s \cdot g^{-1})$ or less, more preferably $2000(10^{-7} \cdot cm^3 \cdot s \cdot g^{-1})$ or less. In case where the SFC is more than $3000(10^{-7} \cdot cm^3 \cdot s \cdot g^{-1})$ and the water absorbent resin particles having such SFC are used in the water absorbing agent, liquid leakage may occur in the absorbent core.

The extractable polymer content of the water absorbent resin particles according to the present embodiment is preferably 35 mass % or more, more preferably 25 mass % or more, still more preferably 15 mass % or more. A lower limit of the extractable polymer content is most preferably 0 mass %. In case where the extractable polymer content exceeds 35 mass %, the gel strength and the liquid permeability may be low. Further, in case where the water absorbent resin particles are used in the absorbent core, it may be impossible to obtain the water absorbing agent whose re-wet amount is small when a pressure is exerted onto the water absorbing agent.

(2) Compound (Organic Surface Additive) Having (i) a Reactive Group for a Functional Group of a Surface of Each Water Absorbent Resin Particle and (ii) a Hydrophobic Group In the water absorbing agent according to the present invention, the compound (organic surface additive) having (i) a reactive group for a functional group of a surface of each water absorbent resin particle and (ii) a hydrophobic group exists on the surface of the water absorbent resin particle. Further, the hydrophobic group contains a hydrocarbon group whose carbon number is 8 or more, and the compound is represented by the following expression, $13 \leq$(an average carbon number of the hydrocarbon group whose carbon number is 8 or more+the number of primary to tertiary amine nitrogen atoms)$\leq 26$ where the number of the primary to tertiary amine nitrogen atoms$\geq 0$, a ratio of an oxyalkylene group in a molecular mass of the compound is 0 or more and 25 mass % or less, and at least part of the reactive group has a bond to the functional group of the surface of the water absorbent resin particle and/or forms a bond to the functional group at the time of water absorption. Note that, the "average carbon number" refers to a carbon number calculated in accordance with a mass average. Further, the "average" means not only (i) an average of carbon numbers of a hydrocarbon group included in each of plural hydrophobic groups of the compound and has the carbon number of 8 or more in case where the plural hydrophobic groups are included in a molecule of the compound but also (ii) an average of carbon numbers of a hydrocarbon group included in each hydrophobic group of each compound and has the carbon number of 8 or more in case where a mixture of the compounds which are uneven in a carbon number is used as the foregoing compound.

Further, the surface of the water absorbent resin particle is a portion of the water absorbent resin particle which portion is exposed to ambient air and/or a portion extending from an external top of the water absorbent resin particle toward an internal portion whose depth is 1/10 relative to the particle diameter (major axis). Herein, the major axis is a length corresponding to a maximum distance between two points arbitrarily picked up from the surface (portion exposed to ambient air) of each particle.

The compound (organic surface additive) exists on a surface of each water absorbent resin particle, that is, the compound exists between the water absorbent resin particles, so that it is possible to improve the SFC of the water absorbing agent of the present invention. In other words, it is possible to improve the liquid permeability of the water absorbing agent. Note that, in order to improve the liquid permeability, the compound (organic surface additive) having (i) a reactive group for a functional group of a surface of each water absorbent resin particle and (ii) a hydrophobic group has only to be contained in the portion at which the water absorbent resin particle is exposed to ambient air and/or in the portion extending from an external top of the water absorbent resin particle toward an internal portion whose depth is 1/10 relative to a particle diameter (major axis), but it is possible to further improve the properties of the water absorbing agent by incorporating the compound into the portion of the water absorbent resin particle which portion is exposed to ambient air.

Further, in the present invention, the compound having (i) a reactive group for a functional group of a surface of each water absorbent resin particle and (ii) a hydrophobic group exists on the surface of the water absorbent resin particle, so that it is possible to decrease a blocking ratio of the water absorbing agent. Thus, it is possible to improve the flowability when the water absorbing agent absorbs moisture. Note that, in order to improve the flowability at the time of moisture absorption, the compound having (i) a reactive group for a functional group of a surface of each water absorbent resin particle and (ii) a hydrophobic group has only to be contained in the portion of the water absorbent resin particle which portion is exposed to ambient air and/or in the portion extending from an external top of the water absorbent resin particle toward an internal portion whose depth is 1/10 relative to a particle diameter (major axis), but it is possible to further improve the properties of the water absorbing agent by incorporating the compound into the portion of the water absorbent resin particle which portion is exposed to ambient air.

It is preferable that, in the compound having (i) a reactive group for a functional group of a surface of each water absorbent resin particle and (ii) a hydrophobic group, the hydrophobic group contains a hydrocarbon group whose carbon number is 8 or more. It is preferable that the compound (organic surface additive) is represented by the following expression, $$13 \leq (\text{an average carbon number of the hydrocarbon group whose carbon number is 8 or more} + \text{the number of primary to tertiary amine nitrogen atoms}) \leq 26$$

where the number of the primary to tertiary amine nitrogen atoms $\geq 0$, a ratio of an oxyalkylene group in a molecular mass of the compound is 0 or more and 25 mass % or less. The compound (organic surface additive) can effectively exhibit hydrophobic interaction in the compound in case where the number of carbons of a hydrocarbon group having eight carbon atoms or more in its single molecule and the number of nitrogen atoms of primary to tertiary amines are represented by the foregoing expression.

Herein, (an average carbon number of the hydrocarbon group whose carbon number is 8 or more+the number of primary to tertiary amine nitrogen atoms), that is, a total number of an average carbon number of the hydrocarbon group whose carbon number is 8 or more and the number of primary to tertiary amine nitrogen atoms is preferably 13 or more and 26 or less, more preferably 14 or more and 25 or less, still more preferably 16 or more and 24 or less. If the total number of an average carbon number of the hydrocarbon group whose carbon number is 8 or more and the number of primary to tertiary amine nitrogen atoms is set within the foregoing range, the hydrophobic interaction by the hydrocarbon group can effectively act.

Note that, the aforementioned surface cross-linking agent partially includes the same compound as that of the organic surface additive. In the present invention, an agent added mainly in order to improve the water absorbing agent's absorbency against pressure by cross-linking reaction with the surface of the water absorbent resin particle is referred to as "surface cross-linking agent". Further, an agent which exists between the water absorbent resin particles with it partially reacting with a functional group of a surface of each water absorbent resin particle (with it having a bond to a functional group of the surface of the water absorbent resin particle and/or with it forming a bond to a functional group of a surface of each water absorbent resin particle at the time of water absorption) and which is added mainly in order to improve liquid permeability of the water absorbing agent is referred to as "compound having (i) a reactive group for a functional group of a surface of each water absorbent resin particle and (ii) a hydrophobic group (i.e., an organic surface additive)". In this manner, agents are discriminated from each other in accordance with an object and effect thereof. In the present specification, a mixture of the surface cross-linking agent and the organic surface additive is referred to also as "surface treating agent".

In the compound (organic surface additive) having (i) a reactive group for a functional group of a surface of each water absorbent resin particle and (ii) a hydrophobic group, the reactive group for a functional group of a surface of each water absorbent resin particle is not particularly limited. However, it is preferable to include at least one kind selected from amino group and/or salt thereof, two or more hydroxyl groups existing in a single molecule, glycidyl group, cyclic carbonate group, cyclic urethane group, cyclic urea group, and amineoxide group. Each of these reactive groups allows the organic surface additive to have a bond to the functional group of the surface of the water absorbent resin particle and/or to form the bond at the time of water absorption.

Further, it is preferable that the hydrophobic group has a hydrocarbon chain whose carbon number is 8 or more. Although it is only assumption, the hydrophobic group is preferably a group which can exhibit hydrophobic interaction in water, for example, the hydrophobic group preferably contains at least one kind selected from polymers whose recurring units respectively have aliphatic hydrocarbon group, aromatic hydrocarbon group, polyoxyalkylene, organopolysiloxane, polyurethane, polyamide, and acrylic ester, and the hydrophobic group has a hydrocarbon chain whose carbon number is 8 or more. Above all, the hydrophobic group contains at least one kind selected from polymers whose recurring units respectively have aliphatic hydrocarbon group, aromatic hydrocarbon group, polyoxyalkylene, organopolysiloxane, polyurethane, polyamide, and acrylic ester, and contains a hydrocarbon chain whose carbon number is more preferably 10 or more, still more preferably 12 or more, particularly preferably 13 or more, most preferably 14 or more.

Above all, the hydrophobic group is more preferably an aliphatic hydrocarbon group containing a hydrocarbon chain whose carbon number is 8 or more or an aromatic hydrocarbon group containing a hydrocarbon chain whose carbon number is 8 or more, still more preferably an aliphatic hydrocarbon group containing a hydrocarbon chain whose carbon number is 13 or more or an aromatic hydrocarbon group containing a hydrocarbon chain whose carbon number is 13 or more, particularly preferably an aliphatic hydrocarbon group containing a hydrocarbon chain whose carbon number is 14 or more or an aromatic hydrocarbon group containing a hydrocarbon chain whose carbon number is 14 or more.

As a result, hydrophobic groups of the compound (organic surface additive) existing between the water absorbent resin particles come together and are stabilized due to the hydrophobic interaction without any dissolution in water. Thus, a void is generated between the water absorbent resin particles, so that the liquid permeability is improved.

The hydrocarbon group, i.e., a preferable form of the hydrophobic group in the present invention, is more specifically constituted of carbon and hydrogen, and its carbon number is preferably 8 or more, more preferably 13 or more, still more preferably 14 or more. Further, its structure may be straight-chain, branched-chain, or cyclic and may be saturated or unsaturated, but it is more preferable that the structure is straight-chain and saturated. As to the length of the hydrocarbon group, the carbon number is preferably 8 to 100, more preferably 10 to 50, still more preferably 12 to 40, further still more preferably 13 to 30, particularly preferably 14 to 26, most preferably 16 to 24, in view of agglomeration property with respect to the saline solution.

Particularly, a smaller amount of hydrocarbon groups are introduced as each hydrocarbon group is longer, and a ratio of a functional group of a surface of each usable water absorbent resin particle, e.g., a ratio of acid group or salt thereof increases, so that it is possible to improve the absorbing performance. Thus, such arrangement is preferable.

Specific examples of the hydrocarbon group whose carbon number is 8 or more include: a hydrocarbon group including a straight-chain or branched-chain saturated alkyl group such as octyl, nonyl, decyl, undecyl, dodecyl, 2-ethyl hexyl, tridecyl, tetradecyl, pentadecyl, hexadecyl, heptadecyl, octadecyl, nanodecyl, eicosyl, heneicosyl, and docosyl; a hydrocarbon group including a cyclic saturated alkyl group such as cyclooctyl; a hydrocarbon group including a straight-chain or branched-chain unsaturated alkenyl group such as octenyl, nonylenyl, decenyl, undecylenyl, dodecylenyl, 2-ethylhexenyl, tridecylenyl, tetradecylenyl, pentadecylenyl, hexadecylenyl, heptadecylenyl, octadecylenyl, nanodecylenyl, eicocylenyl, heneicocylenyl, and dococylenyl; a hydrocarbon group including a cyclic unsaturated alkenyl group such as cyclooctenyl and cyclododecenyl; and the like. Above all, dodecyl, octadecyl, hexadecyl, and tetradecyl are more preferable. Further, particularly in case of using an unsaturated hydrocarbon unit such as undecylenyl group or the like, it is possible to further exhibit such effect that an antibacterial property is given or exhibit similar effect.

Further, it is possible to use a hydrophobic group whose carbon is entirely fluorinated or a hydrophobic group whose carbon is partially fluorinated.

Note that, as the compound having the hydrophobic group, a compound including a single hydrophobic group may be solely used, or a combination of plural kinds of compounds having different hydrophobic groups may be used.

Further, it is preferable that a ratio of an oxyalkylene group in a molecular mass of the compound (organic surface additive) is 0 mass % or more and 25 mass % or less. A ratio of an oxyalkylene group having alkyleneoxide such as ethyleneoxide and propyleneoxide, relative to a molecular mass of the compound, is preferably 0 or more and 25 mass % or less, more preferably 0 or more and 20 mass % or less, still more preferably 0 or more and 10 mass % or less, particularly preferably 0. If the ratio of an oxyalkylene group in the molecular mass of the compound is 25 mass % or less, it is possible to exhibit hydrophobic interaction effect of hydrophobic groups in the compound.

Further, it is preferable that at least part of the reactive group has a bond to a functional group of a surface of each water absorbent resin particle and/or forms a bond to the functional group at the time of water absorption. Herein, the bond means not only a bond which requires no heating but also a bond formed by heating.

It is preferable that the bond which requires no heating in the present invention is an ionic bond. Further, it is preferable that the bond formed by heating is a covalent bond.

Further, it is more preferable that at least part of the reactive group has a covalent bond and/or an ionic bond to a functional group of a surface of each water absorbent resin particle and/or forms an ionic bond to the functional group at the time of water absorption.

The mechanism for exhibiting the effect in causing the water absorbing agent of the present invention to absorb aqueous liquid has not been specifically found, but it is preferable that part of the organic surface additive having the above-specified reactive group and the specific hydrophobic group forms a bond to a functional group of a surface of each water absorbent resin particle so as to improve the liquid permeability. In order to realize this condition, a rate of a reaction of the organic surface additive with respect to the water absorbent resin particles does not have to be 100%, and it is preferable that 10% or more and less than 100% of the organic surface additive reacts, and it is more preferable that 20% or more and 90% or less of the organic surface additive reacts.

As an index indicative of the rate of a reaction, it is preferable to extract 0.001 mass % or more and less than 1 mass %, preferably, 0.01 mass % or more and less than 1 mass % of the organic surface additive relative to the water absorbing agent by rinsing the water absorbing agent including the water absorbent resin particles and the organic surface additive with ethanol. The amount of the extracted organic surface additive is more preferably 0.05 mass % or more and 0.95 mass % or less. The extraction of the amount within the aforementioned range causes the organic surface additive to exist between the water absorbent resin particles under an optimal condition in the practical use, so that the liquid permeability is greatly improved.

(2-1) Compound Having a Reactive Group Forming a Bond, which Requires No Heating, to the Surface of Each Water Absorbent Resin Particle As described above, the bond between the reactive group and the surface of each water absorbent resin means also the bond which requires no heating. Herein, the wording "requires no heating" means that the compound and the water absorbent resin particles are mixed at a temperature lower than 100° C. and the mixture is kept at the temperature lower than 100° C. The bond formed under such condition is preferably an ionic bond. It is preferable that at least part of the reactive group has an ionic bond to a functional group of a surface of each water absorbent resin particle and/or forms an ionic bond to the functional group at the time of water absorption.

Herein, the ionic bond means a chemical bond which is formed by electrostatic attraction between a cation and an anion. The ionic bond may be formed in case where amine and carboxyl group are positioned close to each other.

Examples of the compound having a reactive group forming a bond, which requires no heating, to the surface of each water absorbent resin particle include: aliphatic amine whose carbon number is 8 to 100; denatured silicone oil; amine acryl polymer or similar acryl polymer; cation emulsion; and the like.

Any aliphatic amine may be used as the foregoing aliphatic amine as long as the carbon number of the aliphatic amine is 8 to 100, but more preferable examples thereof include: aliphatic monoamine whose carbon number is 8 to 26; aliphatic diamine whose carbon number is 8 to 26; aliphatic primary diamine whose carbon number is 8 to 26; secondary amine having at least one aliphatic hydrocarbon group whose carbon number is 8 to 26; tertiary amine having at least one aliphatic hydrocarbon group whose carbon number is 8 to 26; and the like. The hydrocarbon group of the aliphatic amine may be straight-chain, branched-chain, or cyclic and may be saturated or unsaturated, but it is possible to favorably use: straight-chain hydrocarbon monoamine whose carbon number is 8 to 26; straight-chain hydrocarbon diamine whose carbon number is 8 to 26; alkyl primary amine whose carbon number is 8 to 26; dialkyl secondary amine whose carbon number is 8 to 26; secondary amine having one or two alkyl groups each of which has a carbon number of 8 to 26; tertiary amine having one or more alkyl groups each of which has a carbon number of 8 to 26; and the like. Further, the carbon number of the aliphatic amine is preferably 8 to 26, but more preferably 10 to 26, still more preferably 12 to 26, particularly preferably 13 to 26.

More specific examples of the aliphatic amine include: dodecyl amine such as laurylamine; hexadecyl amine such as tridecyl amine, tetradecyl amine, pentadecyl amine, and cetyl amine; octadecyl amine such as heptadecyl amine and stearyl amine; octadecenyl amine such as oleyl amine, coconut amine, tallowate amine; stearylpropylene diamine and/or salt thereof. Further, examples of the salt include: organic salt such as acetate, malate, and propionate; inorganic salt such as hydrochloride, hydrosulfate, and phosphate.

Further, it is possible to use: amine acryl polymer or similar acryl polymer such as amino denatured silicone, epoxy denatured silicone, Polyment (registered trademark: product of NIPPON SHOKUBAI CO., LTD.); and cation emulsion (preferably, Polyment SK-1000 and the like).

Further, it is preferable to arrange the water absorbing agent according to the present invention so as to include, as the water absorbent resin particles, water absorbent resin particles made of polyacrylic acid (salt) cross-linked polymer. That is, it is preferable that the functional group of the surface of the water absorbent resin particle is a carboxyl group. In this case, it is more preferable that the compound, above all, is at least one selected from the aliphatic amines, i.e., primary amine, secondary amine, and tertiary amine, in view of such condition that hydrophobic groups in the compound are greatly hydrophobic and hydrophobic interaction of the hydrophobic groups effectively acts and in view of such condition that interaction with the carboxyl group on the water absorbent resin particle is likely to act. In this case, the aliphatic amine forms an ionic bond to the carboxyl group serving as the functional group of the surface of the water absorbent resin particle at the time of water absorption.

As described above, it is particularly preferable that the bond which requires no heating of the compound is formed by mixing water absorbent resin having a carboxyl group with primary to tertiary aliphatic amines (and/or salt thereof) and/or by causing the mixture to absorb water.

(2-2) Compound Having a Reactive Group Forming a Bond, Formed by Heating, to a Surface of Each Water Absorbent Resin Particle As described above, the bond between the reactive group and the surface of the water absorbent resin particle means also a bond formed by heating. Such bond is formed by heating a mixture of the water absorbent resin particles and the compound (organic surface additive). Herein, "heating" is carried out at 120° C. or higher and 240° C. or lower. The bond formed under such condition is preferably a covalent bond. It is preferable that at least part of the reactive group has a covalent bond to the functional group of the surface of the water absorbent resin particle.

Herein, the covalent bond is a chemical bond formed by such condition that a pair of electrons is shared by two atoms.

As the compound, it is favorably use a compound in which at least part of its reactive group has a covalent bond to the surface of the water absorbent resin particle and its hydrophobic group contains a hydrocarbon group whose carbon number is 8 or more and an average carbon number of the hydrocarbon group is 14 or more.

It is preferable that the hydrophobic group of the compound (organic surface additive) contains a hydrocarbon group whose carbon number is 8 or more and an average carbon number of the hydrocarbon group is 14 or more, and the average carbon number of the hydrocarbon group is more preferably 14 to 26, still more preferably 16 to 24. By setting the average carbon number of the hydrocarbon group within the foregoing range, it is possible to cause the hydrophobic interaction of the hydrocarbon group to effectively act.

Further, as the compound, it is possible to favorably use a compound having, as the reactive group, at least one kind selected from: amino group and/or salt thereof; two or more hydroxyl groups existing in a single molecule; glycidyl group; cyclic carbonate group; cyclic urethane group; cyclic urea group; and amine oxide group.

In case where the reactive group and the functional group of the surface of the water absorbent resin particle are heated with them positioned close to each other, a covalent bond therebetween is formed.

More specifically, in case where the compound (organic surface additive) includes hydroxyl groups each of which serves as the reactive group, it is preferable that at least two hydroxyl groups are included, and it is more preferable that a nonionic surfactant is used. Above all, it is particularly preferable to use an aliphatic ester nonionic surfactant or the like whose carbon number is 14 to 100. The aliphatic ester nonionic surfactant is not particularly limited. However, it is more preferable to use at least one kind selected from glycerin fatty acid ester, sorbitan fatty acid ester, polyoxyethylene sorbitan fatty acid ester, polyoxysorbitol fatty acid ester, and sucrose fatty acid ester. Most preferable examples thereof include glycerol monostearate, sorbitan monostearate, and the like, each of which has 0 mass % of oxyalkylene group in its molecular mass.

If there is used a compound having in its molecule two or more hydroxyl groups each of which serves as the reactive group, for example the carboxyl group of the surface of the water absorbent resin particle and the hydroxyl groups form a covalent bond (ester bond) due to heating, so that it is possible to obtain the effect of the present invention. On the other hand, a compound having a single hydroxyl group in its molecule does not allow for the effect of the present invention. This may be caused by such condition that: a large hydrocarbon group in the compound prevents a reaction with the carboxyl group of the surface of the water absorbent resin particle from proceeding, so that it is difficult to form the covalent bond. Thus, in case where the compound (organic surface additive) has hydroxyl groups each of which serves as the reactive group, it is preferable that the compound has at least two hydroxyl groups.

In case where the compound (organic surface additive) has N (nitrogen) atom, it is preferable that the organic surface additive includes at least one reactive group, and it is preferable that the reactive group is amino group and/or salt thereof.

Further, the organic surface additive is the compound in which at least part thereof has (i) a reactive group forming a covalent bond to the functional group of the surface of the water absorbent resin particle and (ii) a hydrophobic group, and it is preferable that the compound includes an amino group and/or salt thereof as the reactive group and also includes, as the hydrophobic group, a hydrocarbon chain which has a bond to N (nitrogen) atom and whose carbon number is 14 or more. Examples of the organic surface additive include not only the compound but also aliphatic amine, amine acrylic polymer or similar acrylic polymer, each of which has a carbon number of 14 to 100, cationic surfactant, ampholytic surfactant, and the like.

Any aliphatic amine may be used as the foregoing aliphatic amine as long as its carbon number is 14 to 100, but more preferable examples thereof include: aliphatic monoamine whose carbon number is 14 to 26; aliphatic diamine whose carbon number is 14 to 26; aliphatic primary amine whose carbon number is 14 to 26; secondary amine having at least one aliphatic hydrocarbon group whose carbon number is 14 to 26; and tertiary amine having at least one aliphatic hydrocarbon group whose carbon number is 14 to 26. The hydrocarbon group of the aliphatic amine may be straight-chain, branched-chain, or cyclic, and may be saturated or unsaturated. Above all, it is possible to more favorably use: straight-chain hydrocarbon monoamine whose carbon number is 14 to 26; straight-chain hydrocarbon diamine whose carbon number is 14 to 26; alkyl primary amine whose carbon number is 14 to 26; dialkyl secondary amine whose carbon number is 14 to 26; secondary amine having one or two alkyl groups each of which has a carbon number of 14 to 26; and tertiary amine having one or more alkyl groups each of which has a carbon number of 14 to 26. Further, the carbon number of the aliphatic amine is preferably 14 to 26, more preferably 14 to 18.

More specific examples of the aliphatic amine include: hexadecyl amine such as tetradecyl amine, pentadecyl amine, and cetyl amine; octadecyl amine such as heptadecyl amine and stearyl amine; octadecenyl amine such as oleyl amine, coconut amine, tallowate amine; stearylpropylene diamine and/or salt thereof. Further, examples of the salt include: organic salt such as acetate; and inorganic salt such as hydrochloride, and hydrosulfate.

As described above, primary to tertiary amines can form both the bond described in (2-1) and the bond described in (2-2). Note that, in case of using the compound having primary to tertiary amines each of which serves as the reactive group, it is more preferable that the compound forms the bond which requires no heating in view of the effect.

Further, in the invention directed to the water absorbing agent including water absorbent resin particles and an organic surface additive wherein the organic surface additive having (i) a reactive group for a functional group of a surface of each water absorbent resin particle and (ii) a hydrophobic group exists on the surface of the water absorbent resin particle and the organic surface additive includes N atom and at least part of the hydrophobic group forms a covalent bond to the functional group of the surface of the water absorbent resin particle and a ratio of an oxyalkylene group in a molecular mass of the organic surface additive is 0 mass % or more and 25 mass % or less and the hydrophobic group includes a hydrocarbon chain which forms a bond to the N atom and whose carbon number is 12 or more, it is preferable that the carbon number of the aliphatic amine is 12 to 100, and it is preferable that a specific lower limit of the carbon number of the aliphatic amine is 12.

Further, any cationic surfactant may be used as the foregoing cationic surfactant as long as the cationic surfactant has the aforementioned specific structure having the reactive group and the hydrophobic group, but preferable examples thereof include: alkyltrimethyl ammonium salt whose carbon number is 14 to 100; dialkyldimethyl ammonium salt whose carbon number is 14 to 100; alkyldimethylbenzyl ammonium salt whose carbon number is 14 to 100; and alkylamine acetate whose carbon number is 14 to 100. Above all, coconut amine acetate is preferable.

Further, preferable examples of the ampholytic surfactant include: alkylamine oxide whose carbon number is 14 to 100; alkylbetaine whose carbon number is 14 to 100; and alkylamino fatty acid salt whose carbon number is 14 to 100. Above all, it is preferable that lauryldimethylamineoxide is included.

(3) Production Method of Water Absorbing Agent

A method according to the present invention for producing a water absorbing agent including water absorbent resin particles, said method comprises the mixing step in which the water absorbent resin particles are mixed with a compound having (i) a reactive group for a functional group of a surface of each water absorbent resin particle and (ii) a hydrophobic group, wherein the hydrophobic group has a hydrocarbon group whose carbon number is 8 or more, and the compound is represented by the following expression, $$13 \leq (\text{an average carbon number of the hydrocarbon group whose carbon number is 8 or more} + \text{the number of primary to tertiary amine nitrogen atoms}) \leq 26,$$

where the number of the primary to tertiary amine nitrogen atoms $\geq 0$, a ratio of an oxyalkylene group in a molecular mass of the compound is 0 or more and 25 mass % or less. The aforementioned item (2) described the reactive group for a functional group of a surface of each water absorbent resin particle, the compound having the hydrophobic group, the hydrophobic group, and the reactive group. Thus, descriptions thereof, are omitted here.

In the method according to the present invention for producing the water absorbing agent, a mixing timing and a mixing condition in the mixing step may be suitably set in accordance with a type of the reactive group and a type of reaction of the reactive group to the functional group of the surface of each water absorbent resin particle and are not particularly limited. As to a mode of the method according to the present invention for producing the water absorbing agent, examples thereof include: a mode in which the mixing step is carried out at a temperature lower than 100° C. and the water absorbing agent is kept at a temperature lower than 100° C. after the mixing step; a mode in which the water absorbing agent is heated after the mixing step; and a similar mode.

(3-1) Mode in which the Mixing Step is Carried Out at a Temperature Lower than 100° C.

The following describes the mode in which the mixing step is carried out at a temperature lower than 100° C. and the water absorbing agent is kept at a temperature lower than 100° C. after the mixing step. In such a mode, the mixing step is carried out at a temperature lower than 100° C. and such a step that the water absorbing agent is heated at a temperature equal to or higher than 100° C. after the mixing step is not performed.

Such a mode is not particularly limited, but it is possible to favorably adopt a method for producing a water absorbing agent in which a compound having (i) a reactive group having an ionic bond to a functional group of a surface of each water absorbent resin particle and/or forming the ionic bond at the time of water absorption and (ii) a hydrophobic group exists on the surface of the water absorbent resin particle.

This makes it possible to produce a water absorbing agent which is excellent in centrifugal retention capacity and saline flow conductivity and which has a low blocking ratio. The mixing step is carried out at a temperature lower than 100° C. and the temperature of the water absorbent resin is not increased thereafter, thereby obtaining the aforementioned effect. This may be based on the following reason: In case of aliphatic amine for example, when it is heated to a temperature equal to or higher than 100° C., the aliphatic amine reacts with the carboxyl group of the surface of the water absorbent resin particle. As a result, an amide bond is formed, which causes a bond position to be fixed, so that the SFC is less improved than the case where the mixing step is carried out at a temperature lower than 100° C. and the water absorbing agent is kept at a temperature lower than 100° C.

Further, it is preferable that the mixing step is carried out at a temperature lower than 100° C. and the water absorbing agent is kept at a temperature lower than 100° C. after the mixing step, but it is more preferable that the mixing step is carried out at a temperature lower than 80° C. and the water absorbing agent is kept at a temperature lower than 80° C. after the mixing step.

Further, in the present production method, it is preferable to use water absorbent resin whose surface is cross-linked. In this case, it is preferable that the mixing step is carried out after the surface cross-linking step in which the vicinity of the surface of the water absorbent resin particle is cross-linked with a surface cross-linking agent. This makes it possible to prevent the water absorbing agent obtained in the mixing step from being heated at a temperature equal to or higher than 100° C. due to the heat at the surface cross-linking step. Note that, in case where the heating temperature at the surface cross-linking step is lower than 100° C., the mixing step may be carried out at least during, before, or after the surface cross-linking treatment with the surface cross-linking agent. Note that, in case of cross-linking the vicinity of the surface of the water absorbent resin particle with the surface cross-linking agent in the method for producing the water absorbing agent, the aforementioned surface cross-linking agent and surface cross-linking method can be adopted as a method for carrying out the surface cross-linking treatment.

In the present production method, the compound having (i) the reactive group for a functional group of a surface of each water absorbent resin particle and (ii) the hydrophobic group may be mixed without any modification, but it is more preferable that the compound in a solution or dispersion liquid state is mixed. This makes it possible to evenly mix the compound.

Herein, the solvent used in case where the compound having the hydrophobic group in a solution state is mixed is not particularly limited, but it is possible to favorably use: alcohol such as ethanol, methanol, propyleneglycol, and glycerin; and organic solvent such as hydrocarbon and polyethyleneglycol. Further, the concentration of the compound in the solution is 10 mass % or more and 90 mass % or less, more preferably 20 mass % or more and 80 mass % or less.

Further, a dispersion medium used in case where the compound having the hydrophobic group is mixed in a dispersion state is not particularly limited, but it is possible to favorably use water and an organic solvent such as alcohol for example. Further, the concentration of the compound in the dispersion liquid is preferably 10 mass % or more and 90 mass % or less, more preferably 20 mass % or more and 80 mass % or less. Besides, water-soluble polymer, surfactant, and the like may be further added as the dispersion liquid.

Further, the compound having (i) the reactive group for the functional group of the surface of the water absorbent resin particle and (ii) the hydrophobic group may be mixed with the water absorbent resin particles so that the compound and an emulsifier were in water as an emulsion state as well as the solution or dispersion liquid state. The emulsifier is not particularly limited, but nonionic surfactant, cationic surfactant, and the like may be used.

In mixing the compound having (i) the reactive group for the functional group of the surface of the water absorbent resin particle and (ii) the hydrophobic group with the water absorbent resin particles, a known stirring device can be used as a specific mixing method. Examples of the stirring device include: a cylindrical mixer, a screw mixer, a screw extruder, a turbulizer, a nauta mixer, a V-shaped mixer, a double-arm kneader, a flow mixer, an air current mixer, a rotary disc mixer, a roll mixer, a convolution mixer, a Lödige mixer, a puddle blender, a ribbon mixer, a rotary blender, a jar tumbler, a plough jar mixer, and a mortar mixer. Each of these stirring devices may be equipped with a heating device for heating the mixture containing the compound having (i) the reactive group for the functional group of the surface of the water absorbent resin particle and (ii) the hydrophobic group and may be equipped with a cooling device for cooling the mixture having been heated by the heating device.

A stirring time in mixing the compound having (i) the reactive group for the functional group of the surface of the water absorbent resin particle and (ii) the hydrophobic group with the water absorbent resin particles is not particularly limited, but is preferably 60 minutes or less, more preferably 30 minutes or less.

Further, in the present production method, it is more preferable to mix the compound having (i) the reactive group for the functional group of the surface of the water absorbent resin particle and (ii) the hydrophobic group with the water absorbent resin particles after mechanically damaging the water absorbent resin particles so that the water absorbent resin particles have an irregularly-pulverized shape. If the water absorbent resin particles have the irregularly-pulverized shape, the compound having (i) the reactive group for the functional group of the surface of the water absorbent resin particle and (ii) the hydrophobic group can be efficiently included, thereby improving the properties of the resultant water absorbing agent.

Herein, "mechanical damage" means to give a physical impact by causing glass, metal, and the like to crush against the water absorbent resin particles. A method for giving the mechanical damage to the water absorbent resin particles is not particularly limited as long as an impact can be given to the water absorbent resin particles. An example thereof is a method in which water absorbent resin particles and glass beads are taken to a glass container and then the glass container is shaken so as to mechanically damage the water absorbent resin particles (paint shaker test described later). Further, examples of the method for giving the mechanical damage to the water absorbent resin particles include: a method in which water absorbent resin particles are placed in a cylindrical container with balls so as to rotate the water absorbent resin particles with the balls (ball mill); a method in which the water absorbent resin particles are stirred in a stirring device equipped with a stirring vane; a method in which the water absorbent resin particles are caused to pass through a puddle dryer (a heating device or a cooling device having a puddle vane); a method in which the water absorbent resin particles are crushed by a crusher; a method in which the water absorbent resin particles are transported by pneumatic transportation; a method in which particles of the water absorbing agent are made to crush against each other or are frictionized.

Further, the present invention is a method in which the compound having (i) the reactive group for the functional group of the surface of the water absorbent resin particle and (ii) the hydrophobic group is added to the water absorbent resin particles preferably after the surface cross-linking step carried out with respect to water absorbent resin particles whose essential monomer is an unsaturated carboxylic acid, so as to improve the liquid permeability of the water absorbing agent.

Also, the present invention is directed to use of the compound having (i) the reactive group for the functional group of the surface of the water absorbent resin particle and (ii) the hydrophobic group which compound is added to the water absorbent resin particles preferably after the surface cross-linking step carried out with respect to water absorbent resin particles whose essential monomer is an unsaturated carboxylic acid, so as to improve the liquid permeability of the water absorbing agent.

(3-2) Method for Heating after the Mixing Step

According to the production method in which heating is carried out after the mixing step, the mixing step may be carried out at the same time as the step of mixing the water absorbent resin particles with the surface cross-linking agent or may be carried out at the agglomeration step, at other mixing step, or at other step, which is carried out after the surface cross-linking step. The mixing step is carried out preferably before the surface cross-linking reaction and/or at the time of the surface cross-linking reaction. Specifically, it is preferable to react the organic surface additive at the same time as the surface cross-linking reaction by adding and mixing a mixture solution of the surface cross-linking agent and the organic surface additive to the water absorbent resin particles and then heating the mixture at the time of the aforementioned surface cross-linking step. By carrying out both the reactions at the same time, it is possible to simplify the steps and realize an optimum surface condition.

The heating temperature is preferably 120° C. or higher and 240° C. or lower, more preferably 150° C. or higher and 200° C. or lower.

The production method is not particularly limited, but the method can be favorably adopted as the method for producing the water absorbing agent in which the compound having (i) the reactive group forming a covalent bond to the functional group of the surface of the water absorbent resin particle and (ii) the hydrophobic group exists on the surface of the water absorbent resin particle.

This makes it possible to produce the water absorbing agent which is excellent in centrifugal retention capacity and saline flow conductivity.

Further, it is preferable that the mixing step is carried out at a temperature lower than 100° C. and the resultant is heated at a temperature equal to or higher than 120° C. after the mixture. Further, it is more preferable that the mixing step is carried out at a temperature lower than 80° C. and the resultant is heated at a temperature equal to or higher than 150° C.

An amount of the organic surface additive is preferably 0.001 mass % or more and 5 mass % or less, more preferably 0.005 mass % or more and 2 mass % or less, particularly preferably 0.01 mass % or more and 1 mass % or less, relative to the water absorbent resin particles.

In the surface cross-linking treatment, a conventionally known method can be adopted, and a conventionally known agent can be adopted as the surface cross-linking agent.

In view of properties, preferable examples thereof include polyhydric alcohol compounds, epoxy compounds, polyamine compounds, condensates of polyamine compounds with haloepoxy compounds, oxazoline compounds, monooxazolidinone compounds, dioxazolidinone compounds, polyoxazolidinone compounds, and alkylene carbonate compounds. Specifically, the surface cross-linking agents described as examples in the specifications of U.S. Pat. Nos. 6,228,930, 6,071,976, and 6,254,990 can be used.

It is more preferable to use polyhydric alcohol other than the aforementioned organic surface additive, e.g., it is more preferable to use 1,4-butanediol, 1,2-propanediol, glycerin, and the like.

In the present production method, the specific organic surface additive having (i) the reactive group for the functional group of the surface of the water absorbent resin particle and (ii) the hydrophobic group may be mixed without any modification, but it is more preferable that the organic surface additive in a solution or dispersion liquid state is mixed. This makes it possible to improve the evenness.

In case of mixing the specific organic surface additive in a solution or dispersion liquid state, a solvent used is not particularly limited. However, it is possible to favorably use: alcohol such as ethanol and methanol; and water, for example. Above all, it is particularly preferable to use water. Further, the concentration of the additive in the solution or dispersion liquid is preferably 0.01 mass % or more and 20 mass % or less, more preferably 0.05 mass % or more and 15 mass % or less.

In mixing the organic surface additive with the water absorbent resin particles, it is possible to use a known stirring device as a specific mixing method. Examples of the stirring device include a puddle blender, a ribbon mixer, a rotary blender, a jar tumbler, a plough jar mixer, and a mortar mixer. Other examples thereof include a cylindrical mixer, a screw mixer, a screw extruder, a turbulizer, a nauta mixer, a V-shaped mixer, a double-arm kneader, a flow mixer, an air current mixer, a rotary disc mixer, a roll mixer, a convolution mixer, a Lödige mixer. As a mixing method, it is possible to adopt a butch-type mixing method, a sequential mixing method, or a combination thereof. It is more preferable to adopt the sequential mixing method in terms of industrial production. A rotational frequency at the time of mixing operation is not particularly limited, but it is preferable to set the rotational frequency so that the water absorbent resin is not damaged. Specifically, the rotational frequency preferably ranges from 1 to 3000 rpm, more preferably from 2 to 500 rpm, still more preferably from 5 to 300 rpm. It is not preferable to set the rotational frequency to be more than 3000 rpm since the water absorbent resin becomes powdery which results in drop of the water absorbing property. Further, when the rotational frequency is less than 1 rpm, the mixing operation is not sufficiently performed, so that it is impossible to obtain the desired liquid permeability. Each of these stirring devices may be equipped with a heating device for heating the mixture containing the water absorbent resin particles and the organic surface additive and may be equipped with a cooling device for cooling the mixture having been heated by the heating device.

A stirring time in mixing the organic surface additive with the water absorbent resin particles is not particularly limited, but is preferably 60 minutes or less, more preferably 30 minutes or less.

Further, in the present production method, it is more preferable to mix the organic surface additive with the water absorbent resin particles after mechanically damaging the water absorbent resin particles so that the water absorbent resin particles have an irregularly-pulverized shape. If the water absorbent resin particles have the irregularly-pulverized shape, the organic surface additive can be efficiently included in the surface of the water absorbent resin particle, thereby improving the properties of the resultant water absorbing agent.

Herein, "mechanical damage" means to give a physical impact by causing glass, metal, and the like to crush against the water absorbent resin particles. A method for giving the mechanical damage to the water absorbent resin particles is not particularly limited as long as an impact can be given to the water absorbent resin particles. An example thereof is a method in which water absorbent resin particles and glass beads are taken to a glass container and then the glass container is shaken so as to mechanically damage the water absorbent resin particles (paint shaker test described later). Further, examples of the method for giving the mechanical damage to the water absorbent resin particles include: a method in which water absorbent resin particles are placed in a cylindrical container with balls so as to rotate the water absorbent resin particles with the balls (ball mill); a method in which the water absorbent resin particles are stirred in a stirring device equipped with a stirring vane; a method in which the water absorbent resin particles are caused to pass through a puddle dryer (a heating device or a cooling device having a puddle vane); a method in which the water absorbent resin particles are crushed by a crusher; a method in which the water absorbent resin particles are transported by pneumatic transportation; a method in which particles of the water absorbing agent are made to crush against each other or are frictionized.

An example of other mixing step is a step of agglomerating the water absorbent resin particles. The agglomeration step is not particularly limited, and a conventionally known agglomeration step can be adopted.

Examples of the agglomeration include: a method in which hot water and fine powder of the water absorbent resin particles are mixed with each other and thus obtained mixture is dried (U.S. Pat. No. 6,228,930); a method in which fine powder of the water absorbent resin particles is mixed with a monomer aqueous solution and thus obtained mixture is polymerized (U.S. Pat. No. 5,264,495); a method in which water is added to fine powder of the water absorbent resin particles and thus obtained mixture is agglomerated at not less than a specific surface pressure (European Patent No. 844270); a method in which fine powder of the water absorbent resin particles is sufficiently swollen so as to form an amorphous gel and thus obtained amorphous gel is dried and pulverized (U.S. Pat. No. 4,950,692); a method in which fine powder of the water absorbent resin particles is mixed with a polymerized gel (U.S. Pat. No. 5,478,879); and a similar method.

In the present invention, the organic surface additive is added to water, and they are mixed with the water absorbent resin particles, and the mixture is heated, thereby exhibiting effect.

Further, also by mixing and heating the organic surface additive of the present invention in mixing a solution of a conventionally known water absorbent resin production method with the water absorbent resin particles, it is possible to exhibit effect.

(4) Water Absorbing Agent

The water absorbing agent according to the present invention includes water absorbent resin particles wherein a compound having (i) a reactive group for a functional group of a surface of each water absorbent resin particle and (ii) a hydrophobic group exists on the surface of the water absorbent resin particle. Note that, the aforementioned item (1) described the water absorbent resin particles, and the aforementioned item (2) described the organic surface additive having (i) the reactive group for a functional group of a surface of each water absorbent resin particle and (ii) a hydrophobic group, and the aforementioned item (3) described the method for producing the water absorbing agent, so that descriptions thereof are omitted here.

A preferable water absorbing agent according to the present invention includes water absorbent resin particles (preferably obtained by cross-linking a water-soluble unsaturated monomer, having an internal cross-linked structure, and subjected to surface cross-linking treatment) and a compound having (i) a reactive group for a functional group of a surface of each water absorbent resin particle and (ii) a hydrophobic group, and it is preferable that the following two bonds caused by the compound exist between the water absorbent resin particles and/or on the surface of the water absorbent resin particle at the time of water absorption. A first bond is an intermolecular bond based on hydrophobic interaction of hydrophobic groups of the aforementioned compound which are identical to and/or different from each other, and a second bond is an ionic bond and/or a covalent bond between the functional group of the surface of the water absorbent resin particle and the reactive group. Formation of these two bonds allows the liquid permeability to be much more remarkably improved than conventional techniques. Further, it is possible to achieve a much lower blocking ratio.

Herein, it is preferable that at least part of the reactive group reacts with the functional group of the surface of the water absorbent resin particle. The reaction has only to be an ionic bond and/or a covalent bond. In case where the reaction is an ionic bond, it is particularly preferable that the ionic bond is formed by primary to tertiary amines and carboxyl group.

Further, in case where there is a covalent bond between at least part of the reactive group and the functional group of the surface of the water absorbent resin particle, it is preferable that the covalent bond is an ester bond and/or an amide bond. As described in the aforementioned item (2), the water absorbing agent is such that at least part of the reactive group of the organic surface additive has a covalent bond to the functional group of the surface of the water absorbent resin particle and a rate of a reaction of the organic surface additive to the water absorbent resin particles is 10% or more and less than 100%. If the water absorbing agent is rinsed with ethanol, 0.001 mass % or more and less than 1 mass %, more preferably 0.01 mass % or more and less than 1 mass % of the organic surface additive relative to the water absorbing agent is extracted. In this manner, the foregoing condition can be confirmed.

Further, a preferable mode of the present invention is described as follows. In case where the organic surface additive has hydroxyl groups each of which serves as the reactive group, it is preferable that the organic surface additive has at least two hydroxyl groups, and it is preferable that the rate of the reaction of the organic surface additive to the water absorbent resin particles is 10 to 90%, and the amount of the organic surface additive extracted in rinsing the water absorbing agent with ethanol is 0.001 to 1.0 mass %, preferably 0.01 to 1.0 mass %, more preferably 0.01 to 0.9 mass %.

Further, in case where the organic surface additive includes N atom, it is preferable that the organic surface additive has at least one reactive group and a hydrophobic group containing a hydrocarbon chain which bonds to the N atom and whose carbon number is 14 or more, and the rate of the reaction of the organic surface additive to the water absorbent resin particles is preferably 50 to 100%, and the amount of the organic surface additive extracted in rinsing the water absorbing agent with ethanol is 0.001 to 1.0 mass %, preferably 0.001 to 0.2 mass %, more preferably 0.01 to 0.2 mass %.

If the rate of the reaction is set within the foregoing range and the amount of the extracted organic surface additive is set within the foregoing range, the surface of the water absorbing agent according to the present invention is under an optimal condition at the time of water absorption, thereby greatly improving the liquid permeability.

Further, in the invention directed to the water absorbing agent including water absorbent resin particles and an organic surface additive, wherein an organic surface additive having (i) a reactive group for a functional group of a surface of each water absorbent resin particle and (ii) a hydrophobic group exists on the surface of the water absorbent resin particle, and the organic surface additive has N atom and at least part of the reactive group has a covalent bond to the functional group of the surface of the water absorbent resin particle, and a ratio of an oxyalkylene group in a molecular mass of the organic surface additive is 0 mass % or more and 25 mass % or less, and the organic surface additive has the hydrophobic group containing a hydrocarbon chain which bonds to the N atom and whose carbon number is 12 or more, it is preferable that the rate of the reaction with respect to the water absorbent resin particles is 50 to 100%, and an amount of the organic surface additive extracted in rinsing the water absorbing agent with ethanol is 0.001 to 1.0 mass %, preferably 0.001 to 0.2 mass %, more preferably 0.01 to 0.2 mass %. These value ranges are preferable.

If the rate of the reaction is set within the foregoing range and the amount of the extracted organic surface additive is set within the foregoing range, the surface of the water absorbing agent is under an optimal condition at the time of water absorption, thereby greatly improving the liquid permeability.

Further, as to the water absorbent resin particles in the water absorbing agent, its mass average particle diameter is 100 μm or more and 600 μm or less, more preferably 200 μm or more and 500 μm or less, still more preferably 300 μm or more and 400 μm or less. In case where the mass average particle diameter is out of the foregoing range, the liquid permeability drops, which may cause an absorption rate of the water absorbing agent to significantly drop. That is, the absorption rate greatly drops, which may result in liquid leakage in being used in a diaper for example.

Further, as to the water absorbent resin particles in the water absorbing agent used in the present invention, the water absorbing agent includes 50 mass % or more, preferably 80 mass % or more of the water absorbent resin particles whose particle diameter is 175 μm or more and 710 μm or less.

Further, as to the water absorbent resin particles in the water absorbing agent, a ratio of particles which can pass through a sieve whose mesh size is 150 μm is preferably 5 mass % or less, more preferably 3 mass % or less, most preferably 1 mass % or less. In case where the ratio of particles which can pass through a sieve whose mesh size is 150 μm exceeds 5 mass %, particles disperse at the time of production of the water absorbing agent. This results in safety and sanitary problem. Further, properties of the resultant absorbent core may drop.

As to the water absorbing agent, a logarithmic standard deviation ($\sigma\zeta$) of a particle diameter distribution is preferably 0.20 or more and 0.50 or less, more preferably 0.30 or more and 0.40 or less. If the logarithmic standard deviation ($\sigma\zeta$) is out of the foregoing range, the liquid permeability drops, which may cause the absorption rate of the absorbent core to significantly drop.

Further, as to the water absorbing agent according to the present invention, specific agents described in the foregoing items (1), (2), and (3) are produced in accordance with specific production methods, thereby remarkably improving its water absorbing ability.

Further, as to the water absorbing agent, its CRC is preferably 5 (g/g) or more, more preferably 15 (g/g) or more, still more preferably 25 (g/g) or more, particularly preferably 28 (g/g) or more. An upper limit thereof is not particularly limited but is preferably 60 (g/g) or less, more preferably 50 (g/g) or less, still more preferably 40 (g/g) or less. In case where the CRC is less than 5 (g/g), an absorption capacity is too small to be used in a sanitary material such as a diaper. Further, in case where the centrifugal retention capacity (CRC) is more than 60 (g/g), it may be impossible to obtain a water absorbing agent which is excellent in a rate at which the water absorbing agent absorbs liquid in being used in an absorbent core.

As to the water absorbing agent according to the present invention, its SFC is preferably $10(\times 10^{-7} \text{ cm}^3 \cdot \text{s} \cdot \text{g}^{-1})$ or more, more preferably $30(\times 10^{-7} \text{ cm}^3 \cdot \text{s} \cdot \text{g}^{-1})$ or more, still more preferably $50(\times 10^{-7} \text{ cm}^3 \cdot \text{s} \cdot \text{g}^{-1})$ or more, still further more preferably $70(\times 10^{-7} \text{ cm}^3 \cdot \text{s} \cdot \text{g}^{-1})$ or more, particularly preferably $100(\times 10^{-7} \text{ cm}^3 \cdot \text{s} \cdot \text{g}^{-1})$ or more, most preferably $150(\times 10^{-7} \text{ cm}^3 \cdot \text{s} \cdot \text{g}^{-1})$ or more. In case where the SFC is less than $10(\times 10^{-7} \text{ cm}^3 \cdot \text{s} \cdot \text{g}^{-1})$, it may be impossible to obtain a water absorbing agent which is excellent in a rate at which the water absorbing agent absorbs liquid in being used in an absorbent core. An upper limit of the SFC is not particularly limited but is preferably $3000(\times 10^{-7} \text{ cm}^3 \cdot \text{s} \cdot \text{g}^{-1})$ or less. If the SFC exceeds this value, this may raise the problem described in the item "Water absorbent resin particles".

As to the water absorbing agent according to the present invention, its absorbency against pressure of 4.83 kPa (i.e., AAP) is preferably 8 (g/g) or more, more preferably 16 (g/g) or more, still more preferably 20 (g/g or more, particularly preferably 22 (g/g) or more, most preferably 24 (g/g) or more. An upper limit thereof is not particularly limited but is preferably 30 (g/g) or less. In case where the absorbency against pressure of 4.83 kPa (i.e., AAP) is less than 8 (g/g), it may be impossible to obtain a water absorbing agent whose re-wet amount is small when a pressure is exerted onto an absorbent core including the water absorbing agent.

An extractable polymer content of the water absorbing agent is preferably 35 mass % or less, more preferably 25 mass % or less, still more preferably 15 mass % or less. A lower limit thereof is preferably 0 mass %. In case where the extractable polymer content of the water absorbing agent exceeds 35 mass %, its gel strength may be low and its liquid permeability may be low. Further, in case where the particulate water absorbing agent is used in a diaper for an extended period of time, the CRC and AAP may drop as time elapses.

A blocking ratio (BR) of the water absorbing agent is preferably 30% or less, more preferably 20% or less, most preferably 10% or less.

Further, it is preferable to give the water absorbing agent of the present invention a hydrophilic property. Examples of a technique for making the water absorbing agent hydrophilic include: a method in which a water absorbent resin containing tetravalent or further polyvalent polyol at least in its surface is used (WO2005/044915); a method in which inorganic fine powder is added to a water absorbent resin and the water absorbent resin is irradiated with UV (Japanese Unexamined Patent Publication Tokukai 2006-233008); a method in which a water absorbing agent composition containing water-insoluble inorganic fine powder and satisfying a specific condition is used (Japanese Patent Application Tokugan 2007-504791); a method in which a water absorbent resin containing water-soluble multivalent metal salt and a urea derivative is used (U.S. Patent Publication No. 2005-0288182; a method in which hydrophilic inorganic fine particles are added (Japanese Patent Application Tokugan 2006-188668); and a similar conventionally known method.

As to the water absorbing agent of the present invention, its surface tension is preferably 30 (mN/m) or more, more preferably 50 (mN/m) or more, still more preferably 70 (mN/m) or more. If the surface tension is less than 30 (mN/m), the re-wet amount of the absorbent core including the water absorbing agent may increase and it may be impossible to obtain the desired performance. Note that, the surface tension is a value measured by a below-described measurement method.

(5) Absorbent Core (Water Absorbent Core)

In the present invention, an absorbent core (water absorbent core) includes the water absorbing agent. A combination of the absorbent core and a suitable material results in a favorable absorbent core serving as an absorbent layer of a sanitary material. The following describes the absorbent core.

The absorbent core is a formed composition, used in sanitary materials such as a disposable diaper, a sanitary napkin, an incontinence pad, a medical pad, to absorb blood, body fluid, and urine. An example of the material used is a cellulose fiber. Specific examples of the cellulose fiber include: wood pulp fibers such as a mechanical pulp, a chemical pulp, a semi-chemical pulp, a dissolved pulp, and the like, that are extracted from wood; artificial cellulose fibers such as rayon and acetate; and the like. Among the cellulose fibers, it is preferable to use the wood pulp fiber. Each of these cellulose fibers may partially contain a synthesis fiber such as nylon and polyester. In case of using the water absorbing agent obtained in the present invention as a part of the absorbent core, a mass of the water absorbing agent obtained in the present invention is preferably 20 mass % or more, more preferably 30 mass % or more, still more preferably 40 mass % or more. When the mass of the water absorbing agent obtained in the present invention is less than 20 mass %, it may be impossible to obtain a sufficient effect.

In order to obtain the absorbent core according to the present invention by using (a) the water absorbing agent and (b) the cellulose fiber, an appropriate method is selected, for example, from the following known methods: a method in which the water absorbing agent is dispersed on paper or a mat made from cellulose fiber and the dispersed water absorbing agent is held by the paper or mat as required; a method in which the cellulose fiber and the water absorbing agent are evenly blended with each other; and a similar method. It is preferable to adopt a method in which the water absorbing agent and the cellulose fiber are dry mixed with each other and then are compressed. According to this method, it is possible to remarkably suppress the water absorbing agent from falling away from the cellulose fiber. It is preferable to perform the compression while heating, and a temperature range at this time is 50 to 200° C. for example.

The water absorbing agent obtained in the present invention is superior in properties. Thus, when the water absorbing agent is used in the absorbent core, it is possible to obtain an extremely superior absorbent core which quickly absorbs liquid and has little liquid remaining on a surface layer thereof.

The water absorbing agent obtained in the present invention has a superior water absorbing property. Thus, the water absorbing agent can be used as a water absorbing/retaining agent in various use. For example, it is possible to use the water absorbing agent in: absorbing article water absorbing/retaining agents such as a disposable diaper, a sanitary napkin, an incontinence pad, and a medical pad; agriculture/horticulture water retaining agents such as an alternative bog moss, a soil reforming/improving agent, a water retaining agent, and an agrichemical effect maintaining agent; architectural water retaining agents such as an interior wall condensation preventing agent, and a cement additive; a release control agent; a cold insulation agent; a disposable body warmer; a sewage coagulator; a food freshness maintaining agent; an ion exchange column material; a sludge or oil dehydrating agent; a desiccating agent; a humidity controlling agent; and the like. Above all, the water absorbing agent according to the present invention is favorably used in an absorbing sanitary material, such as a disposable diaper and a sanitary napkin, which absorbs feces, urine, and blood.

In case where the absorbent core is used in sanitary materials such as a disposable diaper, a sanitary napkin, an incontinence pad, a medical pad, it is preferable to arrange the absorbent core so as to include: (a) a liquid permeable top sheet disposed adjacent to a body of the user, (b) a liquid impermeable back sheet disposed adjacent to a clothe of the user so as to be away from the body of the user, and (c) an absorbent core disposed between the top sheet and the back sheet. The absorbent core may be arranged so as to be two- or-more-layered, or may be used with a pulp layer.

EXAMPLES

The following description specifically explains the present invention, but the present invention is not limited to this. Note that, for convenience in description, "part by mass" is referred to merely as "part", and "litter" is referred to merely as "L". Further, "mass %" is sometimes referred to as "wt %".

Properties of the water absorbent resin particles or the water absorbing agent were measured in accordance with the following method. Further, when a specific condition is not described, this means that all the operations were performed at room temperature. (20 to 25° C.) and at humidity of 50 RH %.

Note that, in case of the water absorbing agent used as a final product such as a sanitary material, the water absorbing agent absorbed moisture, so that the water absorbing agent was separated from the final product as required and properties thereof were measured after being subjected to reduced-pressure low-temperature drying (for example, at 1 mmHg or less and at 60° C. for 12 hours). Further, a solid content of each of the water absorbing agents used in Examples of the present invention and Comparative Examples was 94 mass % or more. Further, the following description explains how to measure the properties of the water absorbing agent as an example, but the same method is applicable also to measurement of properties of the water absorbent resin particles.

<Centrifugal Retention Capacity (CRC)>

The centrifugal retention capacity (CRC) represents an absorption capacity at which 0.90 mass % of saline is absorbed for 30 minutes without any pressure. Note that, the CRC is sometimes referred to as an absorbency without load.

0.200 g of a water absorbing agent was evenly contained in a bag (85 mm×60 mm) made of a nonwoven fabric (Heatron Paper made by Nangoku Pulp Kogyo Co., Ltd.: model type is GSP-22). Then, the bag was heat-sealed. Thereafter, the bag was soaked in an excessively large amount (generally, about 500 ml) of 0.90 mass % physiological saline (sodium chloride aqueous solution) whose temperature had been adjusted to room temperature, and was withdrawn 30 minutes later. By using a centrifugal separator (centrifugal machine made by KOKUSAN Corporation: model type was H-122), the bag was drained for three minutes at a centrifugal force (250 G) recited in edana ABSORBENCY II 441.1-99, and a mass $W_1$ (g) of the bag was measured. Further, the same operation was performed without using the water absorbing agent, and a mass $W_0$ (g) was measured. Then, from the masses $W_1$ and $W_0$, a centrifugal retention capacity (CRC) (g/g) was calculated according to the following equation.

Centrifugal retention capacity (g/g)=(mass $W_1$ (g)−mass $W_0$ (g))/mass (g) of water absorbing agent)−1

<Absorbency Against Pressure of 4.83 kPa (AAP)>

Figure 2:
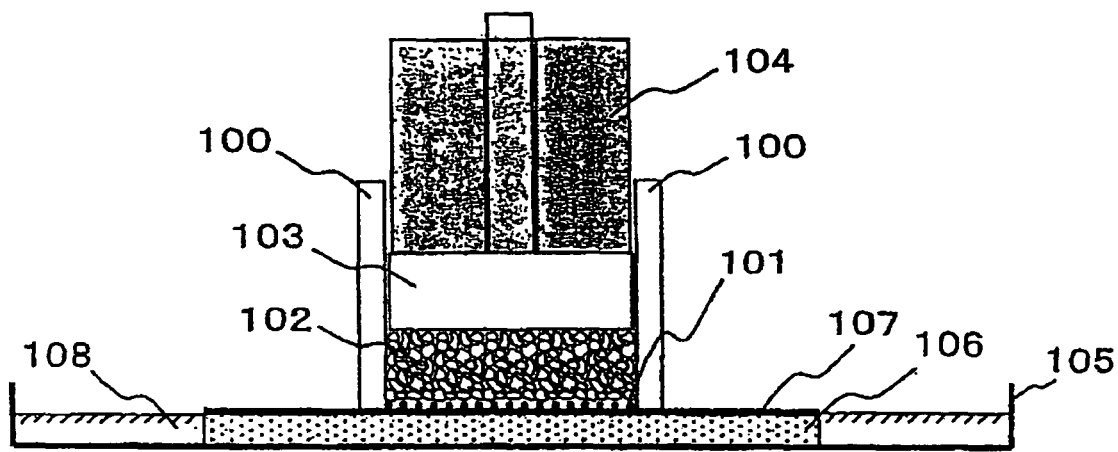
FIG. 2 is a schematic illustrating a measuring apparatus used in measuring AAP in each of Examples.

The absorbency against pressure (AAP) represents an absorbency at which 0.90 mass % of saline is absorbed for 60 minutes at 4.83 kPa. Note that, the AAP is referred to also as an absorbency against pressure of 4.83 kPa. FIG. 2 is a cross sectional view of a measuring apparatus 10.

By using the measuring apparatus 10 shown in FIG. 2, the absorbency against pressure (AAP) was measured. On a bottom of a plastic supporting cylinder 100 having a 60 mm internal diameter, a metal gauze 101 of stainless-steel 400 mesh (mesh size of 38 µm) was fusion-bonded. Then, under a condition of a room temperature (20° C. or higher and 25° C. or lower) and 50 RH % relative humidity, 0.900 g of a water absorbing agent was evenly spread on the gauze 101. Subsequently, a piston 103 and a load 104 were placed in this order on the water absorbing agent serving as a sample 102 so that there is no gap between the piston 103 and the supporting cylinder 100 and upward and downward movements of the piston 103 and the load 104 would not be hampered. Then, a mass Wa (g) of this set of the measuring apparatus 10 was measured.

Inside a petri dish 105 having a 150 mm diameter, a glass filter 106 (product of Sougo Rikagaku Glass Seisakusho Co., Ltd.; diameter of fine pores: 100 µm to 120 µm) having a 90 mm diameter was placed. Thereafter, a 0.90 mass % of sodium chloride solution 108 whose temperature had been adjusted to 20° C. or higher and 25° C. or lower was added until it reached a level of an upper surface of the glass filter 106. Then, a piece of filter paper 107 (product of Advantec Toyo Kaisha, Ltd.; product name: JIS P3801, No. 2; thickness: 0.26 mm; diameter of retained particles: 5 µm) having a 90 mm diameter was placed thereon, so that an entire surface of the filter paper 107 was wetted. An excess of the 0.90 mass % saline 108 was removed.

The set of the measuring apparatus 10 was placed on the wet filter paper 107. Then, the water absorbing agent was made to absorb the 0.90 mass % saline 108 for one hour under the load. One hour later, the set of the measuring apparatus 10 having absorbed the 0.90 mass % saline 108 was lifted, and a mass Wb (g) thereof was measured. From the masses Wa and Wb, the absorbency against pressure (AAP) (g/g) was calculated according to the following equation.

Absorbency against pressure of 4.83 kPa (AAP)=($Wb$ (g)−$Wa$ (g))/mass (0.900) g of water absorbing agent)

<Saline Flow Conductivity (SFC)>

Figure 3:
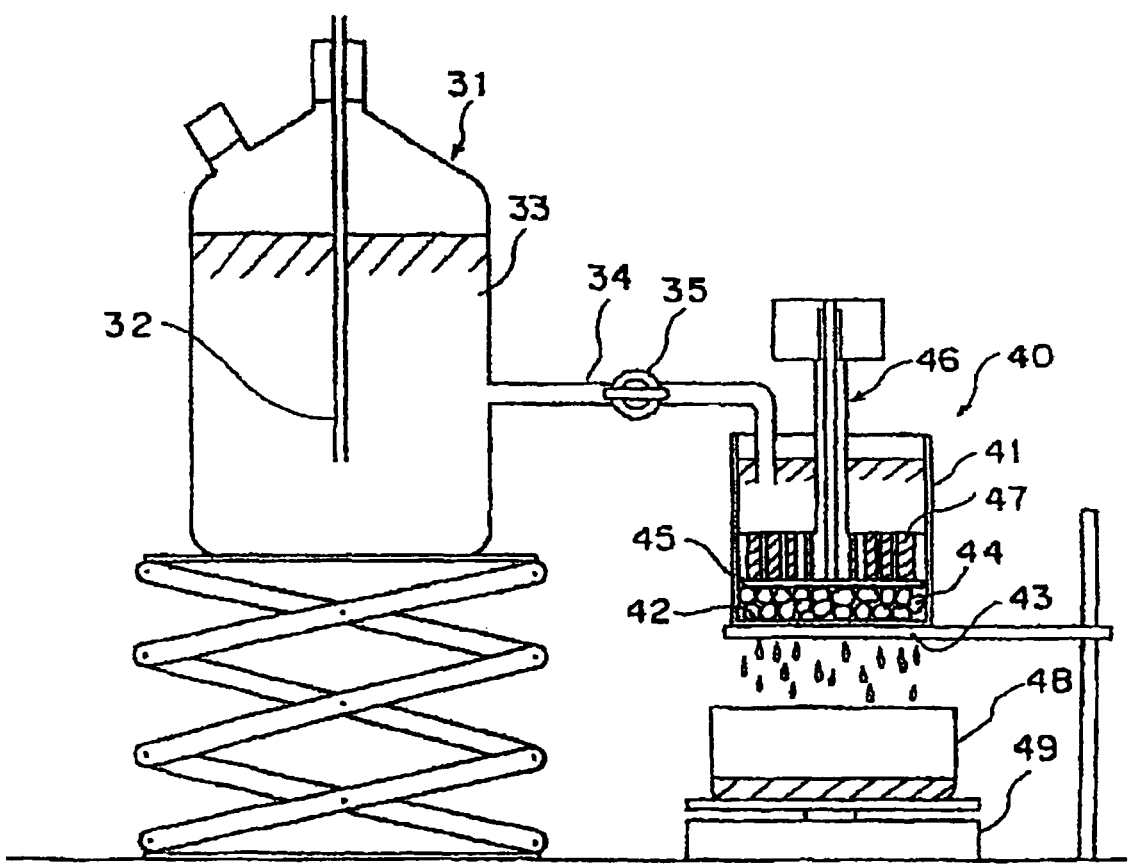
FIG. 3 is a schematic illustrating a measuring apparatus used in measuring SFC in each of Examples.

The saline flow conductivity is a value indicative of liquid permeability when a water absorbing agent is swollen. The higher the SFC is, the higher the liquid permeability is. Calculation of the saline flow conductivity was performed in accordance with a saline flow conductivity (SFC) test described in U.S. Pat. No. 5,849,405. FIG. 3 is a schematic illustrating an SFC measuring apparatus 20.

In the measuring apparatus 20 shown in FIG. 2, a glass tube 32 was inserted into the tank 31, and a lower end of the glass tube 32 was disposed so that 0.69 mass % sodium chloride solution 33 was positioned 5 cm higher than a bottom of the swelling gel 44 in the cell 41. 0.69 mass % sodium chloride solution 33 contained in the tank 31 was supplied to the cell 41 via an L-shaped tube 34 with a cock. A collecting container 48 for collecting liquid having passed through the gel layer was disposed under the cell 41, and the collecting container 48 was placed on an even balance 49. An inside diameter of the cell 41 was 6 cm, and No. 400 stainless metal gauze (38 µm in mesh) 42 was placed on a bottom of a lower portion of the cell 41. A hole 47 which allowed liquid to pass through was provided on a lower portion of a piston 46, and a glass filter 45 having high permeability was provided on the bottom thereof so that the swelling gel did not enter into the hole 47. The cell 41 was placed on a table for the cell, and the table's surface which was in contact with the cell was positioned on the stainless metal gauze 43 which did not prevent the liquid from passing through.

The synthesized urine (1) was prepared by mixing 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of diammonium hydrogen phosphate, and 994.25 g of pure water.

By using the measuring apparatus 20 shown in FIG. 3, the water absorbing agent (0.900 g) evenly spread in a container 40 was swollen in the synthesized urine (1) under a pressure of 2.07 kPa (0.3 psi) for 60 minutes, and a height of a gel layer of a gel 44 was recorded. Then, 0.69 mass % sodium chloride solution 33 was made to flow from a tank 31 and to pass through the swollen gel layer at a constant hydrostatic pressure. The SFC test was performed at room temperature (20° C. or higher and 25° C. lower). By using a computer and a scale, an amount of liquid passing through the gel layer at intervals of 20 seconds was recorded for 10 minutes as a time function. A flow rate Fs(T) of the solution passing through the swollen gel 44 (mainly between particles thereof) was determined in terms of g/s by dividing an increasing weight (g) by an increasing time (s). A time in which a constant hydrostatic pressure and a stable flow rate had been obtained was set as "Ts", and only data obtained between "Ts" and a ten-minute interval was used to calculate the flow rate, the flow rate calculated between "Ts" and a ten-minute interval was used to calculate a value of Fs (T=0), i.e., a first flow rate of the solution passing through the gel layer. Fs (T=0) was calculated by extrapolating T=0 from a result obtained by approximating a function indicative of a relationship between Fs (T) and T.

Saline flow conductivity (SFC)

$= (Fs(t=0) \times L0)/(\rho \times A \times \Delta P)$ $= (Fs(t=0) \times L0)/139506$ Here, Fs (t=0) is a flow rate represented by "g/s", L0 is a height of the gel layer that is represented by "cm", $\rho$ is a density (1.003 g/cm$^3$) of NaCl solution, A is an area (28.27 cm$^2$) on the upper side of the gel layer of the cell 41, $\Delta P$ is a hydrostatic pressure (4920 dyne/cm$^2$) exerted to the gel layer, and a unit of the saline flow conductivity (SFC) is $(10^{-7} \cdot \text{cm}^3 \cdot \text{s} \cdot \text{g}^{-1})$.

In case where liquid permeates so quickly that the hydrostatic pressure does not reach the foregoing level, the SFC can be calculated by changing the $\Delta P$ value to a value calculated by the height of the liquid surface of the physiological saline.

<Mass Average Particle Diameter (D50) and Logarithmic Standard Deviation ($\sigma\zeta$) of Particle Diameter Distribution>

The mass average particle diameter (D50) and the logarithmic standard deviation ($\sigma\zeta$) of particle diameter distribution were measured in accordance with a test on a mass average particle diameter (D50) and logarithmic standard deviation ($\sigma\zeta$) of particle diameter distribution (described in International Publication No. 2004/69915 Pamphlet).

<Ratio of Particles which can Pass Through a Sieve Whose Mesh Size is 150 μm>

The same classification as in the measurement of the mass average particle diameter (D50) and logarithmic standard deviation ($\sigma\zeta$) of particle diameter distribution was carried out so as to calculate the ratio (mass %) of particles which can pass through a sieve whose mesh size is 150 μm.

<Blocking Ratio (BR)>

In the present specification, the blocking ratio is a value obtained at 25° C., at 90 RH %, in an hour.

2.00 g of a water absorbing agent was evenly spread on a bottom of a propylene cup whose inside diameter was 50 mm and height was 10 mm, and was quickly placed in a constant-temperature-and-moisture apparatus (PLATINOOUS LUCIFFER PL-2G, product of TABAI ESPEC CORPORATION) in which temperature had been adjusted to 25° C. and relative humidity had been adjusted to 90%. Then, the water absorbing agent was left in the constant-temperature-and-moisture apparatus for 60 minutes. Thereafter, the water absorbing agent that had absorbed moisture was moved onto a JIS standard sieve (diameter is 7.5 cm, mesh size is 2000 μm), and was sieved for five minutes by using a sieve shaker (IIDA SIEVE SHAKER, TYPE: ES-65, SER. No. 0501). Then, a mass $W_4$ (g) of the water absorbing agent which remained on the sieve and a mass $W_5$ (g) of the water absorbing agent which had passed through the sieve were measured.

Then, the blocking ratio (mass %) was calculated in accordance with the following equation. As the moisture absorption blocking ratio is lower, the water absorbent resin particles or the water absorbing agent is superior in terms of the fluidity at the time of moisture absorption.

Blocking ratio (BR) (mass %)=mass $W_4$ (g)/(mass $W_4$ (g)+mass $W_5$ (g))×100

<Extractable Polymer Content (Quantity of Water-Soluble Component)>

184.3 g of a 0.90 mass % saline was measured and poured into a 250 ml plastic container having a cover. Into the saline, 1.00 g of a water absorbing agent was added, and the saline was stirred for 16 hours by rotating a stirrer, thereby preparing a water-soluble component extract solution. The water-soluble component extract solution was filtered through a piece of filter paper (product of Advantec Toyo Kaisha, Ltd.; product name: JIS P3801, No. 2; thickness: 0.26 mm; diameter of retained particles: 5 μm), thereby obtaining a filtrate. 50.0 g of the filtrate was measured, and used as a measurement solution.

First, only 0.90 mass % of the saline was titrated by using a 0.1N NaOH aqueous solution until pH of the saline reached 10. Thereafter, titration was carried out with 0.1N HCl aqueous solution until pH of the saline reached 2.7, thereby measuring a vacant titration amount ([bNaOH]ml) and a titration amount ([bHCl]ml).

The same titration was performed with respect to the measurement solution, thereby measuring a titration amount ([NaOH]ml) and a titration amount ([HCl]ml).

For example, in case where a water absorbing agent includes a known amount of acrylic acid and sodium chloride thereof, it is possible to calculate, on the basis of an average molecular mass of the monomer and the titration amount obtained in the foregoing operation, a quantity of extractable polymer content in the water absorbing agent in accordance with the following equation. In case of an unknown quantity, an average molecular mass of the monomer is calculated in accordance with a neutralization ratio obtained by the titration.

Quantity of extractable polymer content (mass %)=0.1×(average molecular mass)×184.3×100× ([HCl]−[bHCl])/1000/1.0/50.0

Neutralization ratio (mol %)=(1−([NaOH]−[bNaOH])/ ([HCl]−[bHCl]))×100

<Surface Tension>

80 ml of 0.90 mass % sodium chloride aqueous solution was measured and poured into a 120 ml glass beaker, and 1.00 g of a water absorbing agent was added to the aqueous solution, and the resultant was mildly stirred for 5 minutes. The thus stirred resultant was left still for one minute, and then a surface tension thereof was measured by a plate method. A surface tension of 0.90 mass % physiological saline containing no water absorbing agent was 72 (mN/m).

<Paint Shaker Test>

The paint shaker test (PS) was performed as follows. 10 g of glass beads whose diameter was 6 mm and 30 g of water absorbing agent were placed in a glass container whose diameter was 6 cm and height was 11 cm. Then, the glass container was provided on a paint shaker (product of Toyo Seiki Seisaku-syo, LTD: product No. 488), and was shaken at 800 cycle/min (CPM). An apparatus used in this test is detailed in Japanese Unexamined Patent Publication No. 235378/1997 (Tokukaihei 9-235378).

A test in which a time taken to shake the glass container was 30 minutes was a paint shaker test 1. A test in which a time taken to shake the glass container was 10 minutes was a paint shaker test 2.

After shaking the glass container, the glass beads were removed by using a JIS standard sieve (2 mm in mesh), thereby obtaining a water absorbing agent which had been damaged.

<Rinse of Water Absorbing Agent with Ethanol>

As described in below Example 20 and Comparative Example 24, 8 g of a water absorbing agent was stirred for one hour with 100 g of ethanol (the water absorbing agent and the ethanol were placed in a 100 ml cylindrical sample tube having a cap and the sample tube was rotated at 100 rpm) so as to rinse the water absorbing agent. The ethanol after the rinse was removed from the water absorbent resin (filtered by a 400-mesh SUS metal gauze), and the ethanol after the rinse was heat-dried at 120° C. for three hours, and a mass of the residue was measured, thereby calculating an amount of an unreacted surface treating agent existing on the surface layer having been rinsed with the ethanol. 0.0525 mass % which was a value calculated in Comparative Example 24 (blank: test carried out without using any organic surface additive) was subtracted from the amount of the unreacted surface treating agent existing on the surface layer, thereby calculating a ratio of the unreacted organic surface additive.

<Solid Content of Water Absorbing Agent>

In the water absorbing agent, the solid content is a ratio of a component which do not evaporate at 180° C. A relation between the solid content and a moisture content is as follows.

Solid content (mass %)=100−moisture content (mass %)

The solid content was measured as follows.

About 1 g of a water absorbing agent (mass $W_1$) was measured and placed in an aluminum cup (mass $W_0$) whose bottom diameter was about 5 cm, and the aluminum cup was placed in an airless dryer whose temperature was 180° C. and was left still for three hours so as to dry the water absorbing agent. A mass ($W_2$) of the aluminum cup+the water absorbing agent after the drying was measured, thereby calculating a solid content in accordance with the following equation.

Solid content (mass %)=(($W_2 - W_0$)/$W_1$)×100

Referential Example 1

In a reaction container formed by providing a lid on a 10-litter stainless double-arm kneader equipped with two sigma vanes and a jacket, there was prepared a reaction solution by dissolving 505.6 g of acrylic acid, 4430.8 g of 37 mass % aqueous solution of sodium acrylate, 511.7 g of pure water, and 12.786 g of polyethylene glycol diacrylate (molecular mass of 523). Next, this reaction solution was deaerated under an atmosphere of nitrogen gas for 20 minutes. Subsequently, 14.67 g of 20 mass % aqueous solution of sodium persulfate and 24.45 g of 0.1 mass % aqueous solution of L-ascorbic acid were added thereto under stirred conditions. As a result, polymerization was initiated about 25 seconds after the addition. The polymerization was carried out at 25° C. or higher and 90° C. or lower while the formed gel was crushed. Then, the resultant cross-linked polymer hydrogel was retrieved 30 minutes after the initiation of the polymerization. At this time, a time taken to attain the maximum temperature after the initiation of the polymerization was within 15 minutes. The resultant (hydrogel) cross-linked polymer hydrogel was fragmented into pieces substantially having gel particle diameters of about 5 mm or less.

The fragmented cross-linked polymer hydrogel particles were spread out on a metal gauze of 50 mesh and dried by hot air at 180° C. for 45 minutes. The dried product was pulverized with a roll mill and then classified with JIS standard sieves having mesh sizes of 710 μm and 175 μm, respectively. Fine particles having passed through the sieves were removed, thereby obtaining a water absorbent resin (A), having an irregularly pulverized shape, whose mass average particle diameter (D50) was 343 μm and particle diameter logarithmic standard deviation (σζ) was 0.32. As to the water absorbent resin (A), its centrifugal retention capacity (CRC) was 33.4 (g/g), its extractable polymer content was 6.1 mass %, a ratio of particles which can pass through a sieve of 150 μm mesh was 1.1 mass %.

A surface cross-linking agent made of a mixture solution including 0.3 parts by mass of 1,4-butandiol, 0.5 parts by mass of propyleneglycol, and 2.7 parts by mass of pure water was evenly mixed with 100 parts by mass of the water absorbent resin (A), and the mixture thus obtained was subjected to a heat treatment at 212° C. for 35 minutes. Thereafter, obtained particles were crashed to pass through a JIS standard sieve with 710 μm mesh. Subsequently, the particles having passed through the JIS standard sieve with 710 μm mesh were subjected to a paint shaker test 1. Thus, water absorbent resin particles (1) whose surface was cross-linked were obtained.

Referential Example 2

The same operation as in the Referential Example 1 was carried out except that the heating time after evenly mixing the surface cross-linking agent was changed from 35 minutes to 25 minutes, thereby obtaining water absorbent resin particles (2).

Referential Example 3

In a reaction container formed by providing a lid on a 10-litter stainless double-arm kneader equipped with two sigma vanes and a jacket, there was prepared a reaction solution by dissolving 436.4 g of acrylic acid, 4617.9 g of 37 mass % aqueous solution of sodium acrylate, 377.5 g of pure water, and 10.13 g of polyethylene glycol diacrylate (molecular mass of 523). Next, this reaction solution was deaerated under an atmosphere of nitrogen gas for 20 minutes. Subsequently, 33.91 g of 10 mass % aqueous solution of sodium persulfate and 24.22 g of 0.1 mass % aqueous solution of L-ascorbic acid were added thereto under stirred conditions. As a result, polymerization was initiated about 25 seconds after the addition. The polymerization was carried out at 25° C. higher and 95° C. or lower while the formed gel was crushed. Then, the resultant cross-linked polymer hydrogel was retrieved 30 minutes after the initiation of the polymerization. At this time, a time taken to attain the maximum temperature after the initiation of the polymerization was within 15 minutes. The resultant hydrogel (cross-linked polymer hydrogel) was fragmented into pieces substantially having gel particle diameters of about 5 mm or less.

The fragmented cross-linked polymer hydrogel particles were spread out on a metal gauze of 50 mesh and dried by hot air at 180° C. for 45 minutes. The dried product was pulverized with a roll mill and then classified with JIS standard sieves having mesh sizes of 710 μm and 175 μm, respectively. Fine particles having passed through the sieves were removed, thereby obtaining a water absorbent resin (B), having an irregularly pulverized shape, whose mass average particle diameter (D50) was 340 μm and particle diameter logarithmic standard deviation (σζ) was 0.33. As to the water absorbent resin (B), its centrifugal retention capacity (CRC) was 34.7 (g/g), its extractable polymer content was 7.5 mass %, a ratio of particles which can pass through a sieve of 150 μm mesh was 1.6 mass %.

A surface cross-linking agent made of a mixture solution including 0.38 parts by mass of 1,4-butandiol, 0.63 parts by mass of propyleneglycol, 3.39 parts by mass of pure water, and 0.1 part by mass of sodium persulfate was evenly mixed with 100 parts by mass of the water absorbent resin (B), and the mixture thus obtained was subjected to a heat treatment at 212° C. for 50 minutes. Thereafter, obtained particles were crashed to pass through a JIS standard sieve with 710 μm mesh. Subsequently, the particles having passed through the JIS standard sieve with 710 μm mesh were subjected to a paint shaker test 1. Thus, water absorbent resin particles (3) whose surface was cross-linked were obtained.

Referential Example 4

A solution (A) was prepared by mixing 257.6 g of acrylic acid, 1.31 g (0.07 mol %) of polyethylene glycol diacrylate (molecular mass of 523), and 1.58 g of 1.0 mass % diethylenetriamine penta acetic acid penta sodium salt aqueous solution with each other (temperature of the solution (A) was 23° C.). Further, a solution (B) was prepared by mixing 215.2 g of 48.5 mass % sodium hydroxide aqueous solution (its temperature was 23° C.) with 219.6 g of ion exchange water whose temperature had been adjusted to 33° C. In a polypropylene container, covered by foam polystyrene serving as a heat insulator, which had an internal diameter of 80 mm and a capacity of 1 litter, the solution (B) was quickly added to the solution (A) in an open manner while being stirred by a magnetic stirrer, thereby obtaining a monomer aqueous solution whose temperature had risen to approximately 102° C. to 105° C. due to heat of neutralization and heat of dissolution.

When the temperature of the monomer aqueous solution was decreased to 95° C., 14.3 g of 3 mass % sodium persulfate aqueous solution was added to thus obtained monomer aqueous solution, and the mixture was stirred for several seconds. Thereafter, the resultant was poured in an open manner into a stainless tray-type container whose surface was heated up to 100° C. by a hot plate (NEO HOTPLATE H1-1000: product of IUCHI SEIEIDO CO., LTD.). The stainless tray-type container was internally coated with teflon (registered trademark), and its bottom size was 250×250 mm and top size was 640×640 mm and height was 50 mm so that its central cross-sectional surface was trapezoid with its top open.

Polymerization was initiated right after the monomer aqueous solution had been poured. The polymerization was promoted while generating vapors and expanding/foaming vertically and horizontally. Thereafter, the resultant dwindled so as to be slightly larger than the bottom size. The expanding/dwindling came to an end within approximately one minute. After the resultant had been left in the container for 4 minutes, a resultant cross-linked polymer hydrogel was removed.

Thus obtained cross-linked polymer hydrogel was crushed by a meat chopper (ROYAL MEAT CHOPPER VR400K: product of IIZUKA KOGYO KABUSHIKIKAISHA) whose dice diameter was 9.5 mm, thereby obtaining a cross-linked polymer hydrogel that had been crushed. An amount of the charged gel was approximately 340 g/min, and the crushing was performed by adding purewater at 48 g/min, concurrently with the charge of the gel. A nonvolatile amount of the gel after the crushing was 50 through 55 mass %.

The fragmented cross-linked polymer hydrogel particles were spread out on a metal gauze of 50 mesh and dried by hot air at 180° C. for 40 minutes. The dried product was pulverized with a roll mill and then classified with JIS standard sieves having mesh sizes of 710 μm and 175 μm, respectively, thereby obtaining a water absorbent resin (C), having an irregularly pulverized shape, whose mass average particle diameter (D50) was 340 μm and particle diameter logarithmic standard deviation (σζ) was 0.32, and a ratio of particles which can pass through a sieve of 150 μm mesh was 0.9 mass %. As to the water absorbent resin (C), its centrifugal retention capacity (CRC) was 39.3 (g/g) and its extractable polymer content was 11.3 mass %.

A surface cross-linking agent made of a mixture solution including 0.31 parts by mass of 1,4-butandiol, 0.49 parts by mass of propyleneglycol, and 2.4 parts by mass of pure water was evenly mixed with 100 parts by mass of the water absorbent resin (C), and the mixture thus obtained was subjected to a heat treatment at 195° C. for 25 to 35 minutes. Thereafter, obtained particles were crashed to pass through a JIS standard sieve with 710 μm mesh. Subsequently, the particles having passed through the JIS standard sieve with 710 μm mesh were subjected to a paint shaker test 1. Thus, water absorbent resin particles whose surface was cross-linked were obtained. Particles obtained by heating the mixture for 25 minutes were water absorbent resin particles (4), and particles obtained by heating the mixture for 30 minutes were water absorbent resin particles (5), and particles obtained by heating the mixture for 35 minutes were water absorbent resin particles (6).

Example 1

2.8 parts by mass of 35.7 mass % methanol dispersion liquid of octadecyl amine (stearyl amine) (Wako Pure Chemical Industries, Ltd.) was added to 100 parts by mass of the water absorbent resin particles (1). The solution was evenly added while stirring the water absorbent resin particles (1). The mixture was left still and dried under an airless condition at 60° C. for 30 minutes. In this manner, a water absorbing agent (1) was obtained.

Example 2

2.1 parts by mass of 47.6 mass % methanol solution of dodecyl amine (lauryl amine) (Wako Pure Chemical Industries, Ltd.: Primary) was added to 100 parts by mass of the water absorbent resin particles (1). The solution was evenly added while stirring the water absorbent resin particles (1). The mixture was left still and dried under an airless condition at 60° C. for 30 minutes. In this manner, a water absorbing agent (2) was obtained.

Example 3

2.0 parts by mass of 50 mass % methanol solution of dodecyl amine (lauryl amine) (TOKYO CHEMICAL INDUSTRY CO., LTD.) was added to 100 parts by mass of the water absorbent resin particles (2). The same operation as in Example 1 was carried out. In this manner, a water absorbing agent (3) was obtained.

Example 4

2.0 parts by mass of 50 mass % methanol solution of 1-aminotridecane (n-tridecyl amine) (TOKYO CHEMICAL INDUSTRY CO., LTD.) was added to 100 parts by mass of the water absorbent resin particles (2). The same operation as in Example 1 was carried out. In this manner, a water absorbing agent (4) was obtained.

Example 5

2.0 parts by mass of 50 mass % methanol solution of hexadecyl amine (cetyl amine) (TOKYO CHEMICAL INDUSTRY CO., LTD.) was added to 100 parts by mass of the water absorbent resin particles (2). The same operation as in Example 1 was carried out. In this manner, a water absorbing agent (5) was obtained.

Example 6

2.8 parts by mass of 35.7 mass % methanol solution of octadecyl amine (stearyl amine) (TOKYO CHEMICAL INDUSTRY CO., LTD.) was added to 100 parts by mass of the water absorbent resin particles (2). The same operation as in Example 1 was carried out. In this manner, a water absorbing agent (6) was obtained.

Example 7

1.0 part by mass of oleyl amine (cis-9-octadecenyl amine in a liquid phase at room temperature) (TOKYO CHEMICAL INDUSTRY CO., LTD.) was added to 100 parts by mass of the water absorbent resin particles (2). The same operation as in Example 1 was carried out. In this manner, a water absorbing agent (7) was obtained.

Example 8

1.0 part by mass of didodecyl amine (produced by SIGMA-ALDRICH: its melting point is 51° C.) was added to 100 parts by mass of the water absorbent resin particles (2) having been heated at 90° C. and they were evenly mixed while being melted. The mixture was left still and dried under an airless condition at 60° C. for 30 minutes. In this manner, a water absorbing agent (8) was obtained.

Example 9

1.0 part by mass of Acetamine (registered trademark) 24 (coconut amine acetate) (KAO CORPORATION) was added to 100 parts by mass of the water absorbent resin particles (2). The same operation as in Example 8 was carried out. In this manner, a water absorbing agent (9) was obtained.

Example 10

3.3 parts by mass of FARMIN (registered trademark) DM8098 (dimethylstearyl amine) (KAO CORPORATION) was added to 100 parts by mass of the water absorbent resin particles (3). The same operation as in Example 1 was carried out. In this manner, a water absorbing agent (10) was obtained.

Example 11

3.3 parts by mass of 30 mass % ethanol solution of diamine R-86 (curing tallow propylene diamine) (KAO CORPORATION) was added to 100 parts by mass of the water absorbent resin particles (3). The same operation as in Example 1 was carried out. In this manner, a water absorbing agent (11) was obtained.

Example 12

3.3 parts by mass of 30 mass % ethanol solution of Acetamine (registered trademark) 86 (stearyl amine acetate) (KAO CORPORATION) was added to 100 parts by mass of the water absorbent resin particles (3). The same operation as in Example 1 was carried out. In this manner, a water absorbing agent (12) was obtained.

Example 13

The same operation as in Example 1 was carried out except that the water absorbent resin particles (4) were used instead of the water absorbent resin particles (1). In this manner, a water absorbing agent (13) was obtained.

Example 14

The same operation as in Example 1 was carried out except that the water absorbent resin particles (5) were used instead of the water absorbent resin particles (1). In this manner, a water absorbing agent (14) was obtained.

Example 15

The same operation as in Example 1 was carried out except that the water absorbent resin particles (6) were used instead of the water absorbent resin particles (1). In this manner, a water absorbing agent (15) was obtained.

Example 16

0.28 parts by mass of 35.7 mass % methanol solution of octadecyl amine (stearyl amine) (TOKYO CHEMICAL INDUSTRY CO., LTD.) was added to 100 parts by mass of the water absorbent resin particles (2). The same operation as in Example 1 was carried out. In this manner, a water absorbing agent (16) was obtained.

Comparative Example 1

The water absorbent resin particles (1) were used as a comparative water absorbing agent (1).

Comparative Example 2

1.0 part by mass of paraffin (KANTO CHEMICAL CO., INC.: Primary, its melting point is 58 to 60° C.) heated into a liquid phase at 80° C. was added to 100 parts by mass of the water absorbent resin particles (1) having heated at 60° C. and they were evenly mixed while stirring the water absorbent resin particles (1). The mixture was left still and dried under an airless condition at 60° C. for 30 minutes. In this manner, a water absorbing agent (2) was obtained.

Comparative Example 3

A mixture solution made of 0.80 parts by mass of aluminum sulfate 27.5 mass % aqueous solution (8 mass % as aluminum oxide), 0.134 parts by mass of sodium lactate 60 mass % aqueous solution, and 0.002 mass % of propyleneglycol, was added to 100 parts by mass of the water absorbent resin particles (1) so that the solution was evenly added. The mixture was left still and dried under an airless condition at 60° C. for 30 minutes. In this manner, a comparative water absorbing agent (3) was obtained.

Comparative Example 4

0.3 parts by mass of Aerosil (registered trademark: product of Nippon Aerosil Co. Ltd.) 200 was added to 100 parts by mass of the water absorbent resin particles (1). The addition was carried out while stirring the water absorbent resin particles (1) so that powder was evenly added. The mixture was left still and dried under an airless condition at 60° C. for 30 minutes. In this manner, a comparative water absorbing agent (4) was obtained.

Comparative Example 5

The water absorbent resin particles (2) were used as a comparative water absorbing agent (5).

Comparative Example 6

A mixture solution made of 2.0 parts by mass of aluminum sulfate 27.5 mass % aqueous solution (8 mass % as aluminum oxide), 0.334 parts by mass of sodium lactate 60 mass % aqueous solution, and 0.05 mass % of propyleneglycol, was added to 100 parts by mass of the water absorbent resin particles (2). The addition was carried out while stirring the water absorbent resin particles (2) so that the solution was evenly added. The mixture was left still and dried under an airless condition at 60° C. for 30 minutes. In this manner, a comparative water absorbing agent (6) was obtained.

Comparative Example 7

The water absorbent resin particles (3) were used as a comparative water absorbing agent (7).

Comparative Example 8

The water absorbent resin particles (4) were used as a comparative water absorbing agent (8).

Comparative Example 9

The water absorbent resin particles (5) were used as a comparative water absorbing agent (9).

Comparative Example 10

The water absorbent resin particles (6) were used as a comparative water absorbing agent (10).

Comparative Example 11

1.0 part by mass of Nymeen L-202 (N,N-di(hydroxyethyl) lauryl amine; a ratio of an oxyalkylene group in its molecular mass (hydroxyethyl group is included in an oxyalkylene group) was 31 mass %) (product of Nippon Oil & Fats Co., Ltd.) was added to 100 parts by mass of the water absorbent resin particles (2). The same operation as in Example 1 was carried out. In this manner, a comparative water absorbing agent (11) was obtained.

Comparative Example 12

1.0 part by mass of Nymeen S-204 (polyoxyethylene stearyl amine; a ratio of an oxyalkylene group in its molecular mass was 40 mass %) (product of Nippon Oil & Fats Co., Ltd.) was added to 100 parts by mass of the water absorbent resin particles (2). The same operation as in Example 8 was carried out. In this manner, a comparative water absorbing agent (12) was obtained.

Comparative Example 13

1.0 part by mass of Nymeen S-210 (polyoxyethylene stearyl amine; a ratio of an oxyalkylene group in its molecular mass was 64 mass %) (product of Nippon Oil & Fats Co., Ltd.) was added to 100 parts by mass of the water absorbent resin particles (2). The same operation as in Example 1 was carried out. In this manner, a comparative water absorbing agent (13) was obtained.

Comparative Example 14

1.0 parts by mass of hexyl amine (in a liquid phase at a room temperature; alkyl amine whose alkyl chain has an average carbon number of 6) was added to 100 parts by mass of the water absorbent resin particles (2). The same operation as in Example 1 was carried out. In this manner, a comparative water absorbing agent (14) was obtained.

Comparative Example 15

1.0 part by mass of 1-aminoundecane (in a liquid phase at a room temperature; alkyl amine whose alkyl chain has an average carbon number of 11) was added to 100 parts by mass of the water absorbent resin particles (2). The same operation as in Example 1 was carried out. In this manner, a comparative water absorbing agent (15) was obtained.

Comparative Example 16

1.0 part by mass of 4-phenylbutyl amine (in a liquid phase at a room temperature) was added to 100 parts by mass of the water absorbent resin particles (2). The same operation as in Example 1 was carried out. In this manner, a comparative water absorbing agent (16) was obtained.

Comparative Example 17

1.0 part by mass of dihexyl amine (in a liquid phase at a room temperature; dialkyl amine whose alkyl chain has an average carbon number of 6) was added to 100 parts by mass of the water absorbent resin particles (2). The same operation as in Example 1 was carried out. In this manner, a comparative water absorbing agent (17) was obtained.

The CRCs, SFCs, and BRs of the water absorbing agents (1) to (2) and the comparative water absorbing agents (1) to (4) are shown in Table 1.

The CRCs, SFCs, and BRs of the water absorbing agents (3) to (16) and the comparative water absorbing agents (5) to (17) are shown in Table 1.

A relation between each of the CRCs and each of the SFCs of the water absorbing agents (1) to (16) and the comparative water absorbing agents (1) to (17) is shown in FIG. 1. Note that, in this figure, an X axis indicates the CRC and a Y axis indicates the SFC.

TABLE 1

| | Water absorbing agent | Water absorbent resin particles (precursor) | Additive | CRC (g/g) | SFC (10−7 · cm3 · s · g−1) | BR (%) |
|---|---|---|---|---|---|---|
| Ex. 1 | Water absorbing agent (1) | Water absorbent resin particles (1) | octadecyl amine(*1) | 26.6 | 381 | 0 |
| Ex. 2 | Water absorbing agent (2) | Water absorbent resin particles (1) | dodecyl amine | 26.9 | 123 | 10 |
| Ex. 3 | Water absorbing agent (3) | Water absorbent resin particles (2) | dodecyl amine | 29.0 | 56 | 12 |
| Ex. 4 | Water absorbing agent (4) | Water absorbent resin particles (2) | 1-amino tridecane | 29.2 | 95 | 10 |
| Ex. 5 | Water absorbing agent (5) | Water absorbent resin particles (2) | hexadecyl amine | 29.2 | 90 | 0 |
| Ex. 6 | Water absorbing agent (6) | Water absorbent resin particles (2) | octadecyl amine | 29.0 | 138 | 0 |
| Ex. 7 | Water absorbing agent (7) | Water absorbent resin particles (2) | oleyl amine | 29.6 | 112 | 0 |
| Ex. 8 | Water absorbing agent (8) | Water absorbent resin particles (2) | didodecyl amine | 29.6 | 90 | 0 |
| Ex. 9 | Water absorbing agent (9) | Water absorbent resin particles (2) | acetamine 24 | 29.3 | 83 | — |
| Ex. 10 | Water absorbing agent (10) | Water absorbent resin particles (3) | FARMIN DM8098 | 26.9 | 191 | 0 |
| Ex. 11 | Water absorbing agent (11) | Water absorbent resin particles (3) | diamine R-86 | 26.7 | 141 | 0 |
| Ex. 12 | Water absorbing agent (12) | Water absorbent resin particles (3) | acetamine 86 | 26.9 | 146 | — |
| Ex. 13 | Water absorbing agent (13) | Water absorbent resin particles (4) | octadecyl amine(*1) | 31.4 | 49 | 0 |
| Ex. 14 | Water absorbing agent (14) | Water absorbent resin particles (5) | octadecyl amine(*1) | 30.2 | 115 | 0 |

TABLE 1-continued

| | | Water absorbent resin particles (precursor) | Additive | CRC (g/g) | SFC (10−7 · cm3 · s · g−1) | BR (%) |
|---|---|---|---|---|---|---|
| Ex. 15 | Water absorbing agent (15) | Water absorbent resin particles (6) | octadecyl amine(*1) | 29.0 | 163 | 0 |
| Ex. 16 | Water absorbing agent (16) | Water absorbent resin particles (2) | octadecyl amine(*1) | 29.0 | 80 | — |
| C. Ex. 1 | Comparative Water absorbing agent (1) | Water absorbent resin particles (1) | no additive | 27.0 | 63 | 100 |
| C. Ex. 2 | Comparative Water absorbing agent (2) | Water absorbent resin particles (1) | paraffine | 26.7 | 50 | 40 |
| C. Ex. 3 | Comparative Water absorbing agent (3) | Water absorbent resin particles (1) | aluminum sulfate* | 26.6 | 118 | 73 |
| C. Ex. 4 | Comparative Water absorbing agent (4) | Water absorbent resin particles (1) | Aerosil 200 | 26.7 | 119 | 56 |
| C. Ex. 5 | Comparative Water absorbing agent (5) | Water absorbent resin particles (2) | no additive | 29.2 | 25 | 100 |
| C. Ex. 6 | Comparative Water absorbing agent (6) | Water absorbent resin particles (2) | aluminum sulfate* | 28.9 | 45 | 50 |
| C. Ex. 7 | Comparative Water absorbing agent (7) | Water absorbent resin particles (3) | no additive | 26.9 | 86 | 100 |
| C. Ex. 8 | Comparative Water absorbing agent (8) | Water absorbent resin particles (4) | no additive | 31.6 | 9 | 100 |
| C. Ex. 9 | Comparative Water absorbing agent (9) | Water absorbent resin particles (5) | no additive | 30.3 | 25 | 100 |
| C. Ex. 10 | Comparative Water absorbing agent (10) | Water absorbent resin particles (6) | no additive | 29.0 | 40 | 100 |
| C. Ex. 11 | Comparative Water absorbing agent (11) | Water absorbent resin particles (2) | Nymeen L-202 (N-N-di (hydroxyethyl) lauryl amine) | 28.7 | 25 | — |
| C. Ex. 12 | Comparative Water absorbing agent (12) | Water absorbent resin particles (2) | Nymeen S-204 (polyoxy ethylene stearyl amine) | 28.8 | 29 | — |

TABLE 1-continued

|  | Water absorbent resin particles (precursor) | Additive | CRC (g/g) | SFC (10−7 · cm3 · s · g−1) | BR (%) |
|---|---|---|---|---|---|
| C. Ex. 13 | Comparative Water absorbing agent (13) | Water absorbent resin particles (2) | Nymeen S-210 (polyoxy ethylene stearyl amine) | 28.5 | 23 | — |
| C. Ex. 14 | Comparative Water absorbing agent (14) | Water absorbent resin particles (2) | hexyl amine | 29.0 | 26 | — |
| C. Ex. 15 | Comparative Water absorbing agent (15) | Water absorbent resin particles (2) | 1-amino undecane | 29.0 | 35 | — |
| C. Ex. 16 | Comparative Water absorbing agent (16) | Water absorbent resin particles (2) | 4-phenyl butyl amine | 29.0 | 23 | — |
| C. Ex. 17 | Comparative Water absorbing agent (17) | Water absorbent resin particles (2) | dihexyl amine | 29.0 | 26 | — |

Ex: Example
C. Ex: Comparative Example
*aluminum sulfate, sodium lactate, and propyleneglycol are included.
(*1) 1 part by mass
(*2) 0.1 part by mass As illustrated in Table 1 and FIG. 1, the water absorbing agent obtained in each Example of the present invention had an extremely high saline flow conductivity (SFC) under a pressure unlike the water absorbing agent of each Comparative Example though the water absorbing agent of each Example had the same centrifugal retention capacity. Further, the water absorbing agent obtained in each Example of the present invention had a small BR value and showed excellent flowability at the time of moisture absorption.

Referential Example 5

In a reaction container formed by providing a lid on a 10-litter stainless double-arm kneader equipped with two sigma vanes and a jacket, there was prepared a reaction solution by dissolving 505.6 g of acrylic acid, 4430.8 g of 37 mass % aqueous solution of sodium acrylate, 511.7 g of pure water, and 12.786 g of polyethylene glycol diacrylate (molecular mass of 523). Next, this reaction solution was deaerated under an atmosphere of nitrogen gas for 20 minutes. Subsequently, 14.67 g of 20 mass % aqueous solution of sodium persulfate and 24.45 g of 0.1 mass % aqueous solution of L-ascorbic acid were added thereto under stirred conditions. As a result, polymerization was initiated about 25 seconds after the addition. The polymerization was carried out at 25° C. or higher and 90° C. or lower while the formed gel was crushed. Then, the resultant cross-linked polymer hydrogel was retrieved 30 minutes after the initiation of the polymerization. At this time, a time taken to attain the maximum temperature after the initiation of the polymerization was within 15 minutes. The resultant hydrogel (cross-linked polymer hydrogel) was fragmented into pieces substantially having gel particle diameters of about 5 mm or less.

The fragmented cross-linked polymer hydrogel particles were spread out on a metal gauze of 50 mesh and dried by hot air at 180° C. for 45 minutes. The dried product was pulverized with a roll mill and then classified with JIS standard sieves having mesh sizes of 710 µm and 175 µm, respectively. Fine particles having passed through the sieves were removed, thereby obtaining a water absorbent resin (A), having an irregularly pulverized shape, whose mass average particle diameter (D50) was 343 µm and particle diameter logarithmic standard deviation (σζ) was 0.32, and a ratio of particles which can pass through a sieve of 150 µm mesh was 1.1 mass %. As to the water absorbent resin (A), its centrifugal retention capacity (CRC) was 33.4 (g/g), its extractable polymer content was 6.1 mass %, a ratio of particles which can pass through a sieve of 150 µm mesh was 1.0 mass %.

Example 17

A surface cross-linking agent made of a mixture solution including 0.34 parts by mass of 1,4-butandiol, 0.56 parts by mass of propyleneglycol, 3.0 parts by mass of pure water, and 1.0 part by mass of glycerol monostearate (the mixture solution had been heated at 90° C. and was in a bilayer state) was evenly mixed with 100 parts by mass of the water absorbent resin (A) which had been obtained in Referential Example 5 and had been heated at 60° C., and the mixture thus obtained was subjected to a heat treatment at 212° C. for 30 minutes. Thereafter, obtained particles were crashed to pass through a JIS standard sieve with 710 µm mesh, thereby obtaining a water absorbing agent (17-30). The same operation was carried out except that the heating time was changed to 40 minutes. In this manner, a water absorbing agent (17-40) was obtained.

Example 18

The same operation as in Example 17 was carried out except that 1.0 part by mass of coconut amine acetate (Acetamine 24 produced by KAO CORPORATION) instead of 1.0 part by mass of glycerol monostearate, thereby obtaining water absorbing agents (18-30) and (18-40).

Example 19

The same operation as in Example 17 was carried out except that 1.0 part by mass of sorbitan monostearate (RHEODOL SP-S10 produced by KAO CORPORATION) instead of 1.0 part by mass of glycerol monostearate. However, the heating time was changed to 40 minutes and 50 minutes respectively, thereby obtaining water absorbing agents (19-40) and (19-50).

Example 20

The same operation as in Example 17 was carried out except that 1.0 part by mass of stearyl amine (octadecyl amine) instead of 1.0 part by mass of glycerol monostearate. However, the heating time was changed to 40 minutes, thereby obtaining a water absorbing agent (20-40).

Example 21

The same operation as in Example 17 was carried out except that 1.0 part by mass of ethoxylated stearyl amine (Nymeen S202, HLB5.0 produced by Nippon Oil & Fats Co., Ltd.) instead of 1.0 part by mass of glycerol monostearate. However, the heating time was changed to 50 minutes, thereby obtaining a water absorbing agent (21-50).

Example 22

The same operation as in Example 17 was carried out except that the amount of glycerol monostearate was changed from 1.0 part by mass to 0.001 part by mass. However, the heating time was changed to 40 minutes, thereby obtaining a water absorbing agent (22-40).

Example 23

The same operation as in Example 17 was carried out except that the amount of glycerol monostearate was changed from 1.0 part by mass to 0.005 part by mass. However, the heating time was changed to 40 minutes, thereby obtaining a water absorbing agent (23-40).

Example 24

The same operation as in Example 17 was carried out except that the amount of glycerol monostearate was changed from 1.0 part by mass to 0.01 part by mass. However, the heating time was changed to 45 minutes, thereby obtaining a water absorbing agent (24-45).

Comparative Example 18

The same operation as in Example 17 was carried out except that glycerol monostearate was not used. However, the heating time was changed to 20 minutes and 30 minutes respectively, thereby obtaining comparative water absorbing agents (18-30) and (18-40).

Comparative Example 19

The same operation as in Example 17 except that the heating temperature was changed to 60° C. and the heating time was changed to 30 minutes, thereby obtaining a comparative water absorbing agent (19-30).

Comparative Example 20

1.0 part by mass of glycerol monostearate (heated into a liquid phase at 90° C.) was evenly mixed with the comparative water absorbing agent (18-30) obtained in Comparative Example 18. Thereafter, obtained particles were crashed to pass through a JIS standard sieve with 710 μm mesh, thereby obtaining a comparative water absorbing agent (20).

Comparative Example 21

The following operation was carried out with reference to Example 1 of Japanese Translation of PCT International Application Tokuhyo 2004-512165. A surface cross-linking agent made of 0.5 parts by mass of ethylene carbonate, 0.56 parts by mass of propyleneglycol, 2.0 parts by mass of pure water, 8.0 parts by mass of acetone, and 0.1 part by mass of ethoxylated stearyl amine (Nymeen S210, HLB12.8 produced by Nippon Oil & Fats Co., Ltd.) was evenly mixed with 100 parts by mass of the water absorbent resin (A) obtained in Referential Example 5, and then the mixture was heated at 180° C. for 30 minutes. Thereafter, obtained particles were crashed to pass through a JIS standard sieve with 710 μm mesh, thereby obtaining a comparative water absorbing agent (21-30). The same operation was carried out except that the heating time was changed to 40 minutes, thereby obtaining a comparative water absorbing agent (21-40).

Comparative Example 22

The same operation as in Example 17 was carried out except that 1.0 part by mass of diethanolamide laurate (TOHOL N-230X produced by TOHO Chemical Industry Co., LTD.) instead of 1.0 part by mass of glycerol monostearate, thereby obtaining comparative water absorbing agents (22-30) and (22-40).

Comparative Example 23

The same operation as in Example 17 was carried out except that 1.0 part by mass of polyoxyethylene (20EO) sorbitan monostearate (RHEODOL TW-S120 produced by KAO CORPORATION) instead of 1.0 part by mass of glycol monostearate, thereby obtaining comparative water absorbing agents (23-30) and (23-40).

Comparative Example 24

The same operation as in Example 17 was carried out except that 1.0 part by mass of polyoxyethylene (6EO) sorbitan monooleate (RHEODOL TW-O106 produced by KAO CORPORATION) instead of 1.0 part by mass of glycerol monostearate, thereby obtaining comparative water absorbing agents (24-30) and (24-40).

Comparative Example 25

The same operation as in Example 17 was carried out except that 1.0 part by mass of stearyl alcohol was used instead of 1.0 part by mass of glycerol monostearate, thereby obtaining comparative water absorbing agents (25-30) and (25-40).

Comparative Example 26

The same operation as in Example 17 was carried out except that 1.0 part by mass of stearic acid was used instead of 1.0 part by mass of glycerol monostearate, thereby obtaining comparative water absorbing agents (26-30) and (26-40).

Comparative Example 27

The same operation as in Example 17 was carried out except that 1.0 part by mass of sorbitan monococoate (RHEODOL Super SP-L10 produced by KAO CORPORATION) was used instead of 1.0 part by mass of glycerol monostearate, thereby obtaining comparative water absorbing agents (27-30) and (27-40).

Comparative Example 28

The same operation as in Example 17 was carried out except that 1.0 part by mass of N—N-di(hydroxyethyl)lauryl amine (Nymeen L202, HLB6.2 produced by Nippon Oil & Fats Co., Ltd.) was used instead of 1.0 part by mass of glycerol monostearate. However, the heating time was changed to 50 minutes, thereby obtaining a comparative water absorbing agent (28-50).

Results obtained by measuring properties and the like of the water absorbing agents of Examples 17 to 24 are shown in Table 2, and results obtained by measuring properties and the like of the comparative water absorbing agents of Comparative Examples 18 to 27 are shown in Table 3.

TABLE 2

| | Water absorbing agent | Organic surface additive | Ratio of mass of EO group in additive molecule | Heating temperature Heating time | CRC (g/g) | SFC (10−7 · cm3 · s · g−1) | AAP of 4.83 kPa (g/g) | Extracted amount with ethanol (wt %) |
|---|---|---|---|---|---|---|---|---|
| Ex 17 | Water absorbing agent (17-30) | glycerol mono stearate | 0 | 195° C. 30 minutes | 27.8 | 128 | 22.5 | 0.93 |
| | Water absorbing agent (17-40) | glycerol mono stearate | 0 | 195° C. 40 minutes | 25.7 | 140 | 21.9 | |
| Ex 18 | Water absorbing agent (18-30) | coconut amine acetate (acetamine 24) | 0 | 195° C. 30 minutes | 27.9 | 129 | 24.6 | 0.05 |
| | Water absorbing agent (18-40) | coconut amine acetate (acetamine 24) | 0 | 195° C. 40 minutes | 26.4 | 134 | 23.8 | |
| Ex 19 | Water absorbing agent (19-40) | sorbitan mono stearate (RHEODOL SP-S10) | 0 | 195° C. 40 minutes | 26.2 | 125 | 23.0 | — |
| | Water absorbing agent (19-50) | sorbitan mono stearate (RHEODOL SP-S10) | 0 | 195° C. 50 minutes | 25.2 | 160 | 22.0 | |
| Ex 20 | Water absorbing agent (20-40) | Stearyl amine | 0 | 195° C. 40 minutes | 26.4 | 114 | 22.8 | 0.10 |
| Ex 21 | Water absorbing agent (21-50) | ethoxylated stearyl amine (Nymeen S202) | 25 | 195° C. 50 minutes | 25.5 | 126 | 22.6 | |
| Ex 22 | Water absorbing agent (22-40) | glycerol mono stearate (0.001 mass %) | 0 | 195° C. 40 minutes | 28.4 | 96 | 25.1 | |
| Ex 23 | Water absorbing agent (23-40) | glycerol mono stearate (0.005 mass %) | 0 | 195° C. 40 minutes | 27.7 | 110 | 24.8 | |

TABLE 2-continued

| | Water absorbing agent | Organic surface additive | Ratio of mass of EO group in additive molecule | Heating temperature Heating time | CRC (g/g) | SFC (10−7·cm3·s·g−1) | AAP of 4.83 kPa (g/g) | Extracted amount with ethanol (wt %) |
|---|---|---|---|---|---|---|---|---|
| Ex 24 | Water absorbing agent (24-45) | glycerol mono stearate (0.001 mass %) | 0 | 195° C. 45 minutes | 27.3 | 123 | 24.3 | |

Ex: Example
C. Ex: Comparative Example
SFC: $(10^{-7} \cdot cm^3 \cdot s^{-1})$

TABLE 3

| | Water absorbing agent | Organic surface additive | Ratio of mass of EO group in additive molecule | Heating temperature Heating time | CRC (g/g) | SFC (10−7·cm3·s·g−1) | AAP of 4.83 kPa (g/g) | Extracted amount with ethanol (wt %) |
|---|---|---|---|---|---|---|---|---|
| C. Ex 18 | Water absorbing agent (18-30) | no additive | 0 | 195° C. 30 minutes | 27.9 | 60 | 25.2 | 0.05 |
| | Water absorbing agent (18-40) | no additive | 0 | 195° C. 40 minutes | 26.1 | 97 | 24.2 | |
| C. Ex 19 | Water absorbing agent (19-30) | glycerol mono stearate | 0 | 60° C. 30 minutes | 33.0 | 0 | 7.1 | |
| C. Ex 20 | Water absorbing agent (20) | glycerol mono stearate | 0 | not heated | 27.5 | 55 | 24.2 | |
| C. Ex 21 | Water absorbing agent (21-30) | Ethoxylated stearyl amine (Nymeen S210) | 64 | 180° C. 30 minutes | 28.8 | 62 | 25.8 | 0.97 |
| | Water absorbing agent (21-40) | ethoxylated stearyl amine (Nymeen S210) | 64 | 180° C. 40 minutes | 27.5 | 75 | 24.9 | |
| C. Ex 22 | Water absorbing agent (22-30) | diethanol amide laurate (TOHOL N-230X) | 0 | 195° C. 30 minutes | 27.9 | 46 | 24.8 | 0.96 |
| | Water absorbing agent (22-40) | diethanol amide laurate (TOHOL N-230X) | 0 | 195° C. 40 minutes | 26.1 | 83 | 24.2 | |
| C. Ex 23 | Water absorbing agent (23-30) | polyoxy ethylene (20EO) sorbitan monostearate (RHEODOL TW-S120) | 51 | 195° C. 30 minutes | 27.8 | 41 | 24.8 | |
| | Water absorbing agent (23-40) | polyoxy ethylene (20EO) sorbitan monostearate (RHEODOL TW-S120) | 51 | 195° C. 40 minutes | 26.0 | 63 | 24.0 | |
| C. Ex 24 | Water absorbing agent (24-30) | polyoxy ethylene (6EO) sorbitan monooleate (RHEODOL TW-O106) | 38 | 195° C. 30 minutes | 27.0 | 54 | 24.6 | |

TABLE 3-continued

| | Water absorbing agent | Organic surface additive | Ratio of mass of EO group in additive molecule | Heating temperature Heating time | CRC (g/g) | SFC ($10^{-7} \cdot cm^3 \cdot s \cdot g^{-1}$) | AAP of 4.83 kPa (g/g) | Extracted amount with ethanol (wt %) |
|---|---|---|---|---|---|---|---|---|
| | Water absorbing agent (24-40) | polyoxy ethylene (6EO) sorbitan monooleate (RHEODOL TW-O106) | 38 | 195° C. 40 minutes | 25.6 | 78 | 23.9 | |
| C. Ex 25 | Water absorbing agent (25-30) | stearyl alcohol | 0 | 195° C. 30 minutes | 28.8 | 40 | 25.2 | |
| | Water absorbing agent (25-40) | stearyl alcohol | 0 | 195° C. 40 minutes | 27.1 | 78 | 24.8 | |
| C. Ex 26 | Water absorbing agent (26-30) | stearic acid | 0 | 195° C. 30 minutes | 27.8 | 51 | 24.9 | |
| | Water absorbing agent (26-40) | stearic acid | 0 | 195° C. 40 minutes | 26.5 | 80 | 24.0 | |
| C. Ex 27 | Water absorbing agent (27-30) | sorbitan monococoate (RHEODOL Super SP-L10) | 0 | 195° C. 30 minutes | 28.0 | 60 | 24.4 | |
| | Water absorbing agent (27-40) | sorbitan monococoate (RHEODOL Super SP-L10) | 0 | 195° C. 40 minutes | 27.1 | 85 | 24.0 | |
| C. Ex 28 | Water absorbing agent (28-50) | N,N-di (hydroxyethyl) lauryl amine (Nymeen L-202) | 31 | 195° C. 50 minutes | 25.5 | 90 | 22.1 | |

Ex: Example
C. Ex: Comparative Example
SFC: ($10^{-7} \cdot cm^3 \cdot s \cdot g^{-1}$)

Figure 4:
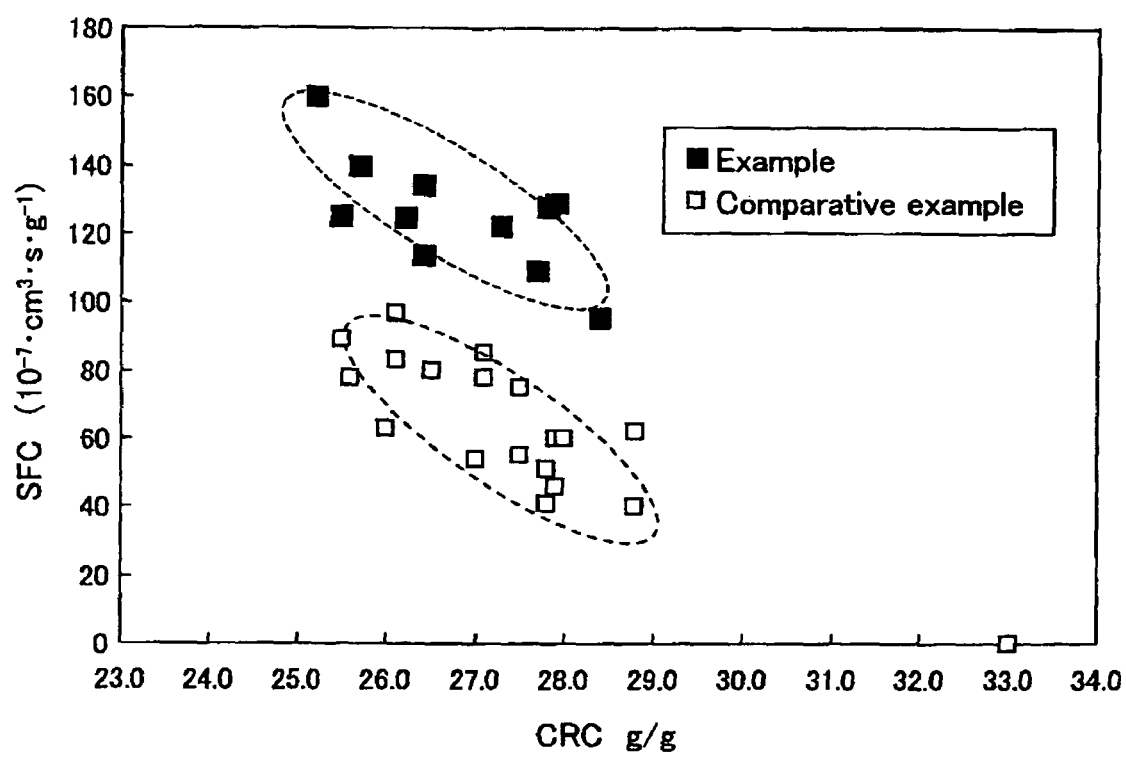
FIG. 4 is a graph illustrating a relation between CRC and SFC of a water absorbing agent obtained in each of Examples and Comparative Examples.

Each of the water absorbing agents obtained in Examples 17 to 24 has more favorable relation between CRC and SFC than those of the comparative water absorbing agents obtained in Comparative Examples 18 to 28 (see FIG. 4).

The result of Comparative Example 18 shows that the performance (relation between CRC and SFC) was low in case where the additive was not used.

The result of Comparative Example 18 shows that the performance (relation between CRC and SFC) was low in case where the reaction temperature was low (60° C.).

The result of Comparative Example 20 shows that mere addition of the organic surface additive (glycerol monostearate) onto the water absorbent resin particles whose surface had been cross-linked resulted in no improvement of the performance.

Thus, a reaction caused by the heat treatment is necessary.

Comparison between Example 21 and Comparative Example 28 and comparison between Example 19 and Comparative Examples 23 and 24 show that ethoxylated alkyl amine or ethoxylated sorbitan fatty acid ester is inferior in the performance (relation between CRC and SFC). This shows that a ratio of an oxyalkylene group in the molecular mass has great influence on the performance. According to the results of Example 21 and Comparative Example 28, the ratio of an oxyalkylene group in the molecular mass is preferably 0 mass % or more and 25 mass % or less. It is most preferable that the ratio is 0 mass %.

Comparative Example 22 shows that the performance (relation between CRC and SFC) is low in case where fatty acid diethanol amide is used as the additive. This may be based on such reason that low reactivity of amide prevents formation of a covalent bond to a carboxyl group.

Comparative Example 25 shows that the performance (relation between CRC and SFC) is higher alcohol is used as the additive. This may be based on the following reason: The higher alcohol has a large alkyl chain for a hydroxyl group, so that the reactivity of the hydroxyl group is low, which prevents formation of a covalent bond to a carboxyl group.

Comparative Example 26 shows that the performance (relation between CRC and SFC) is low in case where a fatty acid is used as the additive.

Comparison between Example 19 and Comparative Example 27 shows that the performance (relation between CRC and SFC) is lower than sorbitan ester whose average carbon number is 18 (sorbitan monostearate) in case where sorbitan ester (sorbitan monococoate) whose average carbon number is about 12 is used as the additive.

Example 25

8 g of the water absorbing agent (17-30) obtained in Example 17 was stirred with 100 ml of ethanol for one hour and was rinsed. The thus rinsed water absorbing agent (17-30) was dried at 120° C. for 5 hours, thereby obtaining a water absorbing agent (25). Ethanol after the rinse was heated and dried at 120° C. for 3 hours, and a mass of a residue thereof was measured, thereby calculating an amount of unreacted surface cross-linking agent existing on the surface rinsed with ethanol. The amount of the unreacted surface cross-linking agent existing on the surface was 0.9292 mass %. 0.0525 mass % calculated in Comparative Example 29 (test carried out without using any additive) was subtracted from the foregoing value, thereby calculating a ratio of the unreacted additive. The amount of the unreacted additive (glycerol monostearate) existing on the surface was 0.8767. Accordingly, the rate of the reaction was 12%.

Comparative Example 29

8 g of the water absorbing agent (18-30) obtained in Example 18 was stirred with 100 ml of ethanol for one hour and was rinsed. The thus rinsed water absorbing agent (18-30) was dried at 120° C. for 5 hours, thereby obtaining a comparative water absorbing agent (29). Ethanol after the rinse was heated and dried at 120° C. for 3 hours, and a mass of a residue thereof was measured, thereby calculating an amount of unreacted surface cross-linking agent existing on the surface rinsed with ethanol. The amount of the unreacted surface cross-linking agent existing on the surface was 0.0525 mass %.

Results obtained by measuring properties of the water absorbing agent obtained in Example 25 and properties of the comparative water absorbing agent obtained in Comparative Example 29 are shown in Table 4.

TABLE 4

| Example | Water absorbing agent | Organic surface additive | Heating temperature Heating time | CRC (g/g) | SFC (10−7 · cm3 · s · g−1) |
|---|---|---|---|---|---|
| Ex 17 | Water absorbing agent (17-30) | glycerol mono stearate | 195° C. 30 minutes | 27.8 | 128 |
| Ex 25 | Water absorbing agent (25) | glycerol mono stearate (after rinse with ethanol) | 195° C. 30 minutes | 27.8 | 84 |
| C. Ex 18 | Comparative water absorbing agent (18-30) | no additive | 195° C. 30 minutes | 27.9 | 60 |
| C. Ex 29 | Comparative water absorbing agent (29) | no additive (after rinse with ethanol) | 195° C. 30 minutes | 27.8 | 58 |

The result of Example 25 shows that existence of the unreacted organic surface additive (herein, glycerol monostearate) on the surface of the water absorbing agent (more specifically, water absorbent resin particles in the water absorbing agent) allows for excellent property (SFC). Further, in Comparative Example 29, the SFC after the rinse with ethanol hardly changed, which shows that existence of the unreacted additive (herein, glycerol monostearate) contributes to improvement of the property.

Comparison between the result of Example 25 and the result of Comparative Example 18 shows that: The additive (herein, glycerol monostearate) bonding to the surface exists also after the rinse with ethanol, so that the water absorbing agent (25) exhibits more excellent SFC than the comparative water absorbing agent (18-30). Further, in case where the heating temperature is low as described in Comparative Example 19 and Comparative Example 20, an esterification reaction of the carboxyl group on the surface of the water absorbent resin particle to the hydroxyl group of the additive does not occur, so that the organic surface additive does not bond. In this case, the SFC was not improved as shown in Table 3. This shows that it is important that at lest part of the organic surface additive bonds to the surface of the water absorbent resin particle in order to improve the SFC as the effect of the present invention. Further, it is preferable that the unreacted additive exists on the surface of the water absorbent resin particle. It is considered that the unreacted product may serve as a binder between hydrophobic groups. However, the effect cannot be obtained by such condition that the organic surface additive merely exists on the surface of the water absorbent resin particle without bonding to the surface.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

| [Reference numerals] | |
|---|---|
| 31 | Tank |
| 32 | Glass tube |
| 33 | 0.69 mass % physiological saline |
| 34 | L-shaped tube with a cock |
| 35 | Cock |
| 40 | Container |
| 41 | Cell |
| 42 | Stainless metal gauze |
| 43 | Stainless metal gauze |
| 44 | Swelling gel |
| 45 | Glass filter |
| 46 | Piston |
| 47 | Hole of piston |
| 48 | Collecting container |
| 49 | Even balance |
| 100 | Plastic supporting cylinder |
| 101 | Stainless 400 mesh metal gauze |
| 102 | Swelling gel |
| 103 | Piston |
| 104 | Load (weight) |
| 105 | Petri dish |
| 106 | Glass filter |
| 107 | Filter paper |
| 108 | 0.9 mass % saline |

INDUSTRIAL APPLICABILITY

The water absorbing agent according to the present invention is excellent in balance between absorbency and liquid permeability against pressure and is excellent in flowability at the time of moisture absorption, so that the water absorbing agent can be used as a water absorbing/retaining agent in various use.

For example, it is possible to use the water absorbing agent in: absorbing article water absorbing/retaining agents such as a disposable diaper, a sanitary napkin, an incontinence pad, and a medical pad; agriculture/horticulture water retaining agents such as an alternative bog moss, a soil reforming/improving agent, a water retaining agent, and an agrichemical effect maintaining agent; architectural water retaining agents such as an interior wall condensation preventing agent, and a cement additive; a release control agent; a cold insulation agent; a disposable body warmer; a sewage coagulator; a food freshness maintaining agent; an ion exchange column material; a sludge or oil dehydrating agent; a desiccating agent; a humidity controlling agent; and the like.

Further, the water absorbing agent of the present invention is particularly favorably used in an absorbing sanitary material, such as a disposable diaper and a sanitary napkin, which absorbs feces, urine, and blood.

What is claimed is:

1. A water absorbing agent, comprising water absorbent resin particles which are surface cross-linked with a polyhydric alcohol, wherein a compound having (i) a reactive group for a functional group of a surface of each water absorbent resin particle and (ii) a hydrophobic group exists on the surface of the water absorbent resin particle, and the hydrophobic group has a hydrocarbon group whose carbon number is 8 or more, and the compound is represented by the following expression, 13≦(an average carbon number of the hydrocarbon group whose carbon number is 8 or more+the number of primary to tertiary amine nitrogen atoms)≦26 where the amount of primary, secondary, or tertiary amine nitrogen atoms ≧0,
a ratio of an oxyalkylene group in a molecular mass of the compound is 0 mass % or more and 25 mass % or less, and at least part of the reactive group bonds to the functional group of the surface of the water absorbent resin particle and/or bonds to the functional group at the time of water absorption; and
wherein the saline flow conductivity of the water absorbent resin particles is $10(\times 10^{-7}\ cm^3 \cdot s \cdot g^{-1})$ or more.

2. The water absorbing agent as set forth in claim 1, wherein the compound is represented by the following expression, 16≦(an average carbon number of the hydrocarbon group whose carbon number is 8 or more+the number of primary to tertiary amine nitrogen atoms)≦24 where the amount of primary, secondary, or to tertiary amine nitrogen atoms ≧0.

3. The water absorbing agent as set forth in claim 1, wherein at least part of the reactive group has an ionic bond to the surface of the water absorbent resin particle and/or forms an ionic bond to the surface of the water absorbent resin particle at the time of water absorption.

4. The water absorbing agent as set forth in claim 3, wherein the water absorbent resin particles and the compound or a solution of the compound or a dispersion liquid of the compound are blended at a temperature lower than 100° C. and are kept at a temperature lower than 100° C.

5. The water absorbing agent as set forth in claim 3, wherein the functional group of the surface of the water absorbent resin particle is a carboxyl group.

6. The water absorbing agent as set forth in claim 3, wherein the compound is at least one selected from primary amine, secondary amine, and tertiary amine.

7. The water absorbing agent as set forth in claim 3, wherein the compound includes a hydrocarbon group whose carbon number is 8 or more and an average carbon number of the hydrocarbon group is 13 to 26.

8. The water absorbing agent as set forth in claim 3, wherein the compound is aliphatic amine.

9. The water absorbing agent as set forth in claim 1, wherein at least part of the reactive group covalently bonds to the surface of the water absorbent resin particle, and the hydrophobic group has a hydrocarbon group whose carbon number is 8 or more, and an average carbon number of the hydrocarbon group is 14 or more.

10. The water absorbing agent as set forth in claim 9, wherein a rate of a reaction of the compound to the water absorbent resin particles is 10% or more and less than 100%.

11. The water absorbing agent as set forth in claim 9, wherein the compound has at least two hydroxyl groups in case where the compound has each hydroxyl group as the reactive group.

12. The water absorbing agent as set forth in claim 9, wherein: in case where the compound has a nitrogen atom, the compound has at least one reactive group and has a hydrophobic group having a hydrocarbon group which bonds to the nitrogen atom and whose average carbon number is 14 or more.

13. The water absorbing agent as set forth in claim 11, wherein the compound is at least one kind selected from aliphatic esterified nonionic surfactants.

14. The water absorbing agent as set forth in claim 12, wherein the compound is at least one kind selected from aliphatic amine, cationic surfactant, and amphoteric surfactant.

15. The water absorbing agent as set forth in claim 1, wherein a mass average particle diameter is 100 μm or more and 600 μm or less and a ratio of particles whose particle diameter is less than 150 μm is 5 mass % or less.

16. The water absorbing agent as set forth in claim 1, wherein the surface of the water absorbent resin particle is cross-linked.

17. The water absorbing agent as set forth in claim 1, wherein an amount of the compound relative to an entire amount of the water absorbing agent is 0.001 mass % or more and 5 mass % or less.

18. A method for producing the water absorbing agent of claim 1, wherein the water absorbing agent comprises water absorbent resin particles, said method comprising the mixing step in which the water absorbent resin particles are mixed with a compound having (i) a reactive group for a functional group of a surface of each water absorbent resin particle and (ii) a hydrophobic group, wherein the hydrophobic group has a hydrocarbon group whose carbon number is 8 or more, and the compound is represented by the following expression, 13≦(an average carbon number of the hydrocarbon group whose carbon number is 8 or more+the number of primary to tertiary amine nitrogen atoms)≦26, where the amount of primary, secondary, or to tertiary amine nitrogen atoms ≧0,
a ratio of an oxyalkylene group in a molecular mass of the compound is 0 or more and 25 mass % or less.

19. The method as set forth in claim 18, wherein at least part of the reactive group has an ionic bond to the functional group of the surface of the water absorbent resin particle and/or forms an ionic bond to the functional group at the time of water absorption, and the mixing step is carried out at a temperature lower than 100° C., and the water absorbing agent is kept at a temperature lower than 100° C. after the mixing step and through completion of production of the water absorbing agent.

20. The method as set forth in claim 19, wherein the mixing step is carried out after a surface cross-linking step in which the vicinity of the surface of the water absorbent resin particle is cross-linked with a surface cross-linking agent.

21. The method as set forth in claim 19, wherein the compound is mixed in a solution or a dispersion liquid.

22. The method as set forth in claim 18, wherein: as said compound, a compound in which at least part of the reactive group has a covalent bond to the surface of the water absorbent resin particle is used, and the water absorbent resin particles and the compound are mixed before and/or during the surface cross-linking, and a temperature at the time of the cross-linking reaction is 120° C. or higher and 240° C. or lower.

23. The method as set forth in claim 22, wherein a polyhydric alcohol which is not equivalent to the compound is mixed at the time of the cross-linking reaction.

24. An absorbent core, comprising the water absorbing agent as set forth in claim 1.

* * * * *